(12) United States Patent
Kinney et al.

(10) Patent No.: US 6,838,594 B1
(45) Date of Patent: Jan. 4, 2005

(54) LIMNANTHES OIL GENES

(75) Inventors: Anthony J. Kinney, Wilmington, DE (US); Steven J. Vollmer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 258 days.

(21) Appl. No.: 09/664,840

(22) Filed: Sep. 19, 2000

Related U.S. Application Data

(63) Continuation of application No. PCT/US99/05471, filed on Mar. 12, 1999.
(60) Provisional application No. 60/078,736, filed on Mar. 20, 1998.

(51) Int. Cl.[7] .......................... A01H 5/00; C12N 15/82; C07H 21/02
(52) U.S. Cl. ...................... 800/298; 800/281; 536/23.2; 536/23.6; 435/468; 435/471; 435/419; 435/252.3
(58) Field of Search ............................. 536/23.2, 23.6; 800/281, 298; 435/69.1, 468, 471, 419, 252.3

(56) References Cited

FOREIGN PATENT DOCUMENTS

| WO | 93/11245 | 6/1993 |
|---|---|---|
| WO | 94/11516 | 5/1994 |
| WO | 96/09394 | 3/1996 |
| WO | 96/24674 | 8/1996 |
| WO | 98/46764 | 10/1998 |

OTHER PUBLICATIONS

Brenner, S.E., TIG 15 (4): 132–133, Apr. 1999.*
Bork et al, TIG 12 (10): 425–427, Oct. 1996.*
Van de Loo et al, PNAS USA 92: 6743–6747, Jul. 1995.*
DeLuca, V, AgBiotech News and Information 5 (6): 225N–229 N, 1993.*
Broun et al, Science 282: 131–133, Nov. 13, 1998.*
Doerks et al, TIG 14 (6): 248–250, Jun. 1998.*
Smith et al, Nature Biotechnology 15: 1222–1223, Nov. 15, 1997.*
Resham S. Bhella et al., Plant Phys., vol. 108:861, 1995, Nucleotide Sequence of a cDNA from Limnanthes douglasil L. Encoding a alpha–15 Linoleic Acid Desaturase.
Clare L. Brough et al., Mol. Breed., vol. 2:133–142, 1996, Towards the genetic engineering of triacylglycerols of defined fatty acid composition: major changes in erucic acid content at the sn–2 position affected by the introduction of a 1–acyl–sn–glycerol–3–phosphate acyltransferase from Limnanthes douglasii into oil seed rape.
Adrian P. Brown et al., Plant Mol. Biol., vol. 29:267–278, 1995, Identification of a cDNA that encodes a 1–acyl–sn–glycerol–3–phosphate acyltransferase from Limnanthese douglasii.

Michael R. Pollard et al., Plant Phys., vol. 66:649–655, 1980, Biosynthesis of C20 and C22 Fatty Acids by Developing Seeds of Limnanthes Alba.
Robert A. Moreau et al., Archives of biochem. and Biophys., vol. 209(2):376–384, Jul. 1981, Properties of a 5–Fatty Acyl–CoA Desaturase in the Cotyledons of Developing Limanthes Alba.
Michael W. Lassner et al., The Plant Cell, vol. 8:281–292, 2/96, A Jojoba beta–Ketoacyl–CoA Synthase cDNA Complements the Canola Fatty Acid Elongation Mutation in Transgenic Plants.
Terry A. Isbell et al., Jaocs, vol. 73(9):10971107, 1996, Mineral Acid–Catalyzed Condensation of Meadowfoam Fatty Acids into Estolides.
Selim M. Erhan et al., Jaocs, vol. 74(5):605–607, 1997, Biodegradation of Estolides from Monounsaturated Fatty Acids.
National Center for Biotechnology Information General Identifier No. 1911477, Mar. 27, 1997, Fukuchi–Mizutani, M. et al., Senescence–induced Expression of a Homologue of Delta 9 Desaturase in Rose Petals.
Masako Fukuchi–Mizutani et al., Plant Mol. Biol., vol. 29:627–635, 1995, Senescence–induced Expression of a Homologue of 9 Desaturase in Rose Petals.
National Center for Biotechnology Information General Identifier No. 2580424, Nov. 5, 1997, Nishida, I.
National Center for Biotechnology Information General Identifier No. 2580425, Dec. 23, 1997, Fukuchi–Mizutani, M. et al., Senescence–induced Expression of a Homologue of Delta 9 Desaturase in Rose Petals.
National Center for Biotechnology Information General Identifier No. 2970034. May 20, 1998, Fukuchi–Mizutani, M. et al., Characterization of delta9 Acyl–Lipid Desaturase Homologues from Arabidopsis Thaliana.
Masako Fukuchi–Mizutani et al., Plant Cell Phys., vol. 39(2):247–253, 1998, Characterization of delta9 Acyl–Lipid Desaturase homologues from Arabidopsis Thaliana.
National Center for Biotechnology Information General Identifier No. 2760830, Jun. 16, 1998, Rounsley, S.D. et al., Arabidopsis Thaliana Chromosome II BAC F18A8 Genomic Sequence.

* cited by examiner

*Primary Examiner*—Elizabeth F. McElwain

(57) ABSTRACT

This invention relates to an isolated nucleic acid fragment encoding an enzyme involved in lipid biosynthesis. The invention also relates to the construction of a chimeric gene encoding all or a portion of the enzyme involved in lipid biosynthesis, in sense or antisense orientation, wherein expression of the chimeric gene results in production of altered levels of the enzyme involved in lipid biosynthesis in a transformed host cell.

15 Claims, 12 Drawing Sheets

```
SEQ ID NO:3                                                    **                 *
SEQ ID NO:2   MSLS----------------------------ASEKEENNKKMAADKAEMG
              LRLSLYFPISISLSLSLEAMASFIATTPAMPAFASVLDPKIPTKPEPKTETPKPKDDLE
              1                                                             60

SEQ ID NO:3           *    ****    *         *    *    ***      *         *
SEQ ID NO:2   R--------KKRAMWERKWKRLDIVKAFASLFVHFLCLLAPFNFTWPALRVALIV--Y
              RFRTSEVVLERKSKGFWRRKWNPRDIQNAVTLLVLHALAAMAPFYFSWDAFWISFILLGF
              61                                                            120

SEQ ID NO:3   *  ****   ****  *  *  *   ****  *****   *       *** **********  *
SEQ ID NO:2   TVGGLGITVSYHRNLAHRSFKVPKWLEYFAYCGLLAIQGDPIDWVSTHRYHHQFTDSDR
              ASGVLGITLCFHRCLTHGGFKLPKLVEYFFAYCGSLALQGDPMEWVSNHRYHHQFVDTER
              121                                                           180

SEQ ID NO:3   * ****  *****   *  ****     *   ***  *  *   * ****   *  ****
SEQ ID NO:2   DPHSPNEGFWFSHLLWLFDTGYLVEK-CGRRTNVEDLKRQWYYKFLQRTVLYHILTFGFL
              DVHSPTQGFWFCHIGWVLDKDLFVEKRGGRRNNVNDLKKQAFYRFLQKTYMYHQLALIAL
              181                                                           240
```

FIG. 2

```
              ***  **        ****   ***  ** ****   *         *     *   ****
SEQ ID NO:3   LYYFGGLSFLTWGMGIGVAMEHHVTCLINSLCHVWGSRTWKTNDTSRNVWWLSVFSFGES
SEQ ID NO:2   LYYVGGFPYIVWGMGFRLVFMFHSTFAINSVCHKWGGRPWNTGDLSTNNMFVALCAFGEG
                                                                        300
              ********* **  **********  **  *  * ****** ****          *
SEQ ID NO:3   WHNNHHAFESSARQGLEWWQIDISWYIVRFLEIIGLATDVKLPSESQRRRM-AMVR
SEQ ID NO:2   WHNNHHAFEQSARHGLEWWQIDVTWYVIRTLQAIGLATNVKLPTEAQKQKLKAKSA
                                                                    356
301
```

FIG. 2 (Continued)

LIMNANTHES OIL GENES

This application is a continuation of International Application No. PCT/US99/05471, filed Mar. 12, 1999, which claims the benefit of U.S. Provisional Application No. 60/078,736 filed Mar. 20, 1998.

FIELD OF THE INVENTION

This invention is in the field of plant molecular biology. More specifically, this invention pertains to nucleic acid fragments encoding enzymes involved in lipid biosynthesis in plants and seeds.

BACKGROUND OF THE INVENTION

Improved means to manipulate fatty acid compositions, from biosynthetic or natural plant sources, are of paramount importance. For example, edible oil sources containing the minimum possible amounts of saturated fatty acids are desired for dietary reasons and alternatives to current sources of highly saturated oil products, such as tropical oils are needed.

Fatty acids are used in plant membranes and in neutral lipids that are formed for energy storage in developing seed tissues. The fatty acid composition (polarity, chain-length and degree of unsaturation) of a membrane determines its physical properties. The most common fatty acids contain 16 or 18 carbons (C16 or C18) with one or more double bonds. Fatty acids with longer (C20 or C22) or shorter (C12 or C14) carbon chains are unusual as are hydroxylated fatty acids and fatty acids with different positions of the double bonds (delta-5 or delta-6). Higher plants appear to synthesize common fatty acids via a metabolic pathway in plant plastid organelles (i.e., chloroplasts, proplastids, or other related organelles) with intermediates bound to acyl carrier proteins as part of the Fatty Acid Synthesis (FAS) complex. The pathways involved in the synthesis of common fatty acids in developing oilseeds are now well understood and are relatively easy to manipulate. In fatty acid biosynthesis, delta-9 acyl-lipid desaturase/delta-9 acyl-CoA desaturase most commonly introduces a double bond at the delta-9 position of a C18 saturated fatty acid (i.e., the desaturation of stearoyl-ACP (C18:0-ACP) to oleoyl-ACP (C18:1-ACP)) to produce mono-unsaturated fatty acids. Several other fatty-acid desaturase enzymes are known in higher plants such as delta-6 and delta-5 desaturases that further desaturate mono-unsaturated fatty acids to make polyunsaturated fatty acids. There are a number of naturally occurring mono-unsaturated fatty acids with double bonds in positions other than the ninth carbon from the fatty acid carboxyl group. For example, the triacylglycerols of *Limnanthes alba* and a number of other gymnosperms all contain mono-unsaturated fatty acids with a double bond at the delta-5 position. This activity may be catalyzed by a delta-5 desaturase that, unlike the delta-9 desaturase which uses 18:1-CoA as a substrate for the desaturation reaction, may instead use 20:0-CoA (Pollard, M. R. and Stumpf, P. K. (1980) *Plant Physiol* 66:649–655; Moreau, R. A. et al. (1981) *Arch Biochem Biophys* 209:376–384).

Meadowfoam (*Limnanthes alba*) is a plant native to the higher elevations of northern California and southern Oregon. The triacylglycerol fraction of the mature seed is composed principally of fatty acids containing 20 or 22 carbons and one or two double bonds (20:1, 22:1 and 22:2). This double bond is unusual in that it is in a position not normally found in the fatty acids of common plant oils: the delta-5 position. The Limnanthes elongase appears to prefer palmitoyl-CoA (16:0-CoA) as its substrate instead of oleoyl-CoA (18:1 delta-9-CoA), the common substrate for the known plant fatty acid elongases. In Limnanthes the 16:0-CoA is elongated to 20:0-CoA and is desaturated to 20:1 delta-5. This is in contrast to the formation of 20:1 delta-11 as in Arabidopsis or Canola where the 18:1 delta-9 is elongated to 20:1 delta-11 (Pollard, M. R. and Stumpf, P. K. (1980) *Plant Physiol* 66:649–655). The genes encoding the Limnanthes delta-5 desaturase and the fatty acyl elongase functions have not been isolated to date and are the subject of the present application.

Although most plants contain at least trace amounts of very long chain fatty acids, the FAS is not involved in the de novo production of these very long chain fatty acids. Instead the products of FAS are exported from the plastid and converted to acyl-CoA derivatives which then serve as the substrates for the fatty acid elongation system (FAE). The gene involved in the Arabidopsis FAE has been localized to the FAE1 locus. The jojoba oil consists mainly of waxes which are esters of monounsaturated fatty acids and alcohols most of which contain fatty acid chains with more than 18 carbons. Elongation to form very long chain fatty acids in Arabidopsis, jojoba and rapeseed uses malonyl-CoA and acyl-CoA as substrates (Lassner, M. W. et al. (1996) *Plant Cell* 8:281–292). In Limnanthes biosynthesis of 20:0 fatty acids occurs predominantly by a chain elongation of palmitate as the initial substrate; thus the enzyme catalyzing this reaction should be similar but yet distinct from the enzyme involved in the production of very long chain fatty acids through the elongation of malonyl-CoA.

The ability to manipulate fatty acid biosynthetic pathways by genetic engineering will allow changes to be made in the fatty acid composition of plant oils and/or to introduce completely new pathways into oilseeds in order to produce novel biopolymers from acetyl-CoA. Limnanthes oils and fatty acids have potential use as industrial agents. Estolides are oligomeric fatty acids containing a secondary ester linkage on the alkyl backbone of the fatty acids. The 20:1 delta-5 fatty acids present in Limnanthes oil are useful for the production of polyestolides where the unique delta-5 bond stabilizes the compound (Isbell, T. A. and Kleiman, R. (1996) *J Am Oil Chem Soc* 73:1097–1107). Biodegradation of polyestiolides derived from the Limnanthes monounsaturated fatty acids appears to be slower than the biodegradation of polyestolides derived from soybean oils or oleic oils but biodegradation continues with time so that all estolides are probably ultimately degraded in nature (Ehran, S. M. and Kleiman, R. (1997) *J Am Oil Chem Soc* 74:605–606). This resistance to bacterial degradation suggests that polyestolides derived from 20:1 delta-5 fatty acids will produce lubricants, greases, plastics, inks, cosmetics and surfactants with a long shelf life.

SUMMARY OF THE INVENTION

The instant invention relates to isolated nucleic acid fragments encoding Limnanthes oil biosynthetic enzymes. Specifically, this invention concerns an isolated nucleic acid fragment encoding a delta-5 acyl-CoA desaturase or a fatty acyl-CoA elongase. In addition, this invention relates to a nucleic acid fragment that is complementary to the nucleic acid fragment encoding a delta-5 acyl-CoA desaturase or fatty acyl-CoA elongase. Also disclosed is the extension of 16:0-CoA to 20:0 by the Limnanthes fatty acyl-CoA elongase. We also show that the delta-5 desaturase, in the absence of 20:0-CoA, will insert a double bond at the delta-5 position of 16:0 and 18:0-CoA.

An additional embodiment of the instant invention pertains to a polypeptide encoding all or a substantial portion of an enzyme involved in lipid biosynthesis selected from the group consisting of a delta-5 acyl-CoA desaturase and fatty acyl-CoA elongase.

In another embodiment, the instant invention relates to a chimeric gene encoding a delta-5 acyl-CoA desaturase or a fatty acyl-CoA elongase, or to a chimeric gene that comprises a nucleic acid fragment that is complementary to a nucleic acid fragment encoding a delta-5 acyl-CoA desaturase or a fatty acyl-CoA elongase, operably linked to suitable regulatory sequences, wherein expression of the chimeric gene results in production of the encoded protein in a transformed host cell.

In a further embodiment, the instant invention concerns a transformed host cell comprising in its genome a chimeric gene encoding a delta-5 acyl-CoA desaturase or a fatty acyl-CoA elongase, operably linked to suitable regulatory sequences. Expression of the chimeric gene results in production of the encoded protein in the transformed host cell. The transformed host cell can be of eukaryotic or prokaryotic origin, and include cells derived from higher plants and microorganisms. The invention also includes transformed embryos and plants that arise from transformed host cells of higher plants, and seeds derived from such transformed plants.

An additional embodiment of the instant invention concerns a method of altering the level of a delta-5 acyl-CoA desaturase or a fatty acyl-CoA elongase in a transformed host cell comprising: a) transforming a host cell with a chimeric gene comprising a nucleic acid fragment encoding a delta-5 acyl-CoA desaturase or a fatty acy-CoAl elongase; and b) growing the transformed host cell under conditions that are suitable for expression of the chimeric gene wherein expression of the chimeric gene results in production of altered levels of a delta-5 acyl-CoA desaturase or a fatty acyl-CoA elongase in the transformed host cell.

An addition embodiment of the instant invention concerns a method for obtaining a nucleic acid fragment encoding all or a substantial portion of an amino acid sequence encoding a delta-5 acyl-CoA desaturase or a fatty acyl-CoA elongase.

In a further embodiment, the instant invention concerns a method for producing a desaturated fatty acid comprising a double bond in the delta-5 position in a host cell, and seeds, oils and methods of producing seed oils wherein the seeds and oils comprise a desaturated fatty acid wherein the fatty acid comprises a double bond in the delta-5 position.

An additional embodiment of the instant invention is a method of reducing the level of 16 carbon fatty acids in a host cell and a method of increasing the level of 20 carbon fatty acids in a host cell, and seeds, oils and methods of producing seed oils with reduced levels of 16 carbon fatty acids or increased levels or 20 carbon fatty acids.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 shows the pathways for the formation of long-chain fatty acids found in Limnanthes seeds. Biosynthesis of palmitate (16:0), stearate (18:0) and oleate (18:1) occurs in the plastid while elongation of palmitate to arachidonate and delta-5 desaturation occurs in the endoplasmic reticulum (adapted from Pollard, M. R. and Stumpf, P. K. (1980) *Plant Physiol* 66:649–655).

FIG. 2 shows an alignment of the amino acid sequences from *Arabidopsis thaliana* delta-9 desaturase (SEQ ID NO:3) and the instant Limnanthes delta-5 acyl-CoA desaturase (lde.pk0008.b9; SEQ ID NO:2). Amino acids which are identical among both sequences are indicated with an asterisk (*) above the alignment. Dashes are used by the program to maximize alignment of the sequences.

Figure 1:
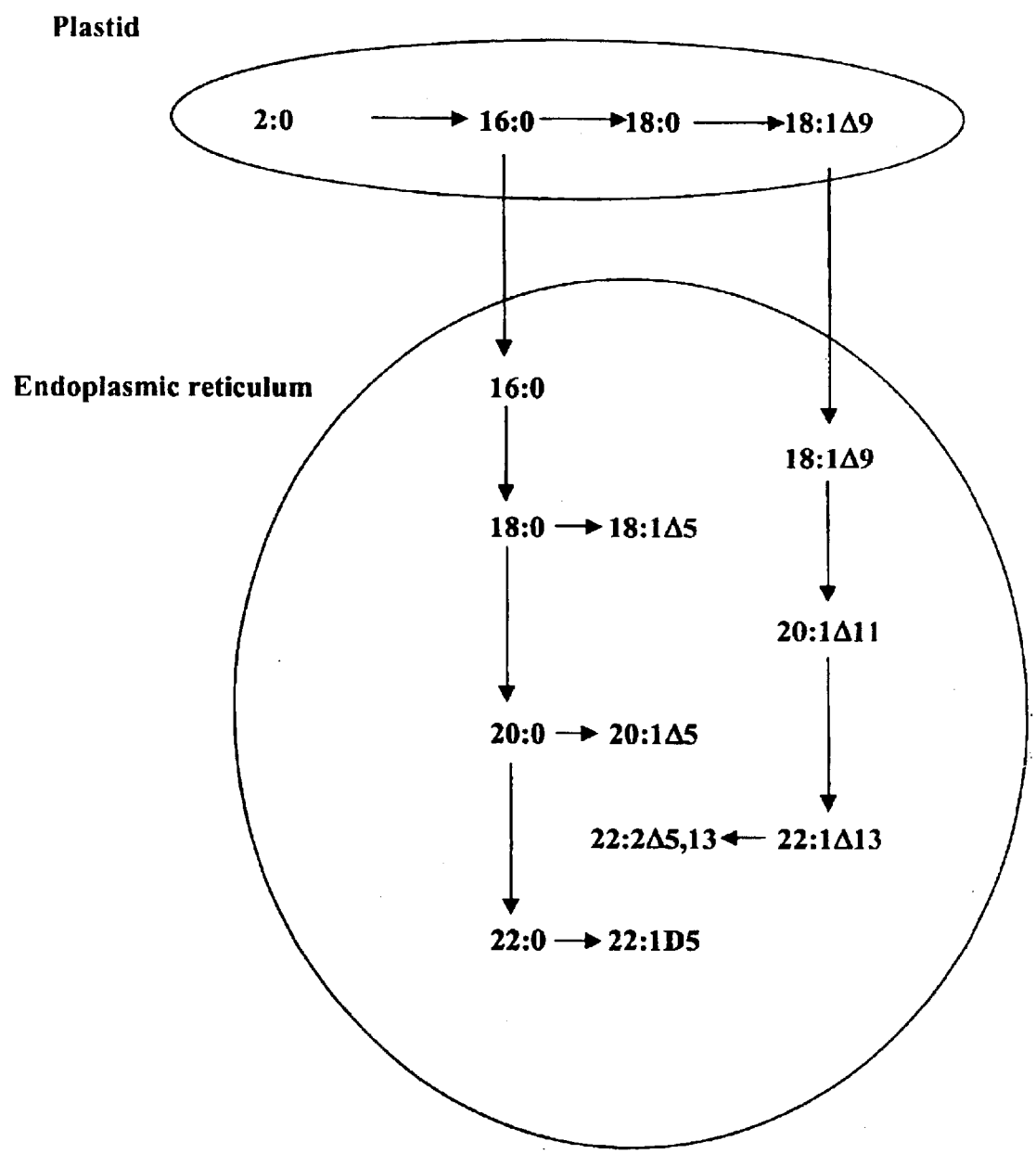

FIG. 6 shows the GC-MS analysis of fatty acid methyl esters prepared from soybean embryos expressing the Limnanthes delta-5 acyl-CoA desaturase demonstrating the formation of 16:1 delta-5 and 18:1 delta-5 fatty acids. FIG. 6(A) presents the gas chromatogram wherein DMDS derivatives of methyl hexadecenoic acid were identified using a selected ion scan for 362 m/z FIG. 6(B) is the mass spectrum of the largest of the two peaks apparent in FIG. 6(A). FIG. 6(C) presents the gas chromatogram wherein DMDS derivatives of methyl octadecenoic acid were identified using a selected ion scan for 390 m/z. FIG. 6(D) is the mass spectrum of the front shoulder of the largest peak that is apparent in FIG. 6(C).

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone lde.pk0008.b9 encoding an entire Limnanthes delta-5 acyl-CoA desaturase.

SEQ ID NO:2 is the deduced amino acid sequence of an entire Limnanthes delta-5 acyl-CoA desaturase derived from the nucleotide sequence of SEQ ID NO:1.

SEQ ID NO:3 is the amino acid sequence of an *Arabidopsis thaliana* delta-9 desaturase having an NCBI General Identifier No:2970034.

SEQ ID NO:4 is the nucleotide sequence comprising the contig assembled from cDNA insert in clones lde.pk0008.d5 and lde.pk0015.d10 encoding an entire Limnanthes fatty acyl-CoA elongase.

SEQ ID NO:5 is the deduced amino acid sequence of an entire Limnanthes fatty acyl-CoA elongase derived from the nucleotide sequence of SEQ ID NO:4.

SEQ ID NO:6 is the nucleotide sequence comprising a portion of the cDNA insert in clone lde.pk0010.e4 encoding a portion of a Limnanthes fatty acyl-CoA elongase.

SEQ ID NO:7 is the deduced amino acid sequence of a portion of a Limnanthes fatty acyl-CoA elongase derived from the nucleotide sequence of SEQ ID NO:6.

The Sequence Listing contains the one letter code for nucleotide sequence characters and the three letter codes for amino acids as defined in conformity with the IUPAC- IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the delta-5 acyl-CoA desaturase or the fatty acyl-CoA elongase proteins as set forth in SEQ ID NOs:2, 5 and 7. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein T M et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of two enzymes involved in lipid biosynthesis have been isolated and identified by comparison of random plant cDNA sequences to public databases containing nucleotide and protein sequences using the BLAST algorithms well known to those skilled in the art. The identity of these enzymes has been confirmed by functional analysis as set forth in Example 6. Table 1 lists the proteins that are described herein, and the designation of the cDNA clones that comprise the nucleic acid fragments encoding these proteins.

TABLE 1

Limnanthes Oil Biosynthetic Enzymes

| Enzyme | Clone | Plant |
| --- | --- | --- |
| Delta-5 Acyl-CoA Desaturase | lde.pk0008.b9 | *Limnanthes douglasii* |
| Fatty Acyl-CoA Elongase | Contig of: lde.pk0008.d5 lde.pk0015.d10 | *Limnanthes douglasii* |
| | lde.pk0010.e4 | *Limnanthes douglasii* |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other delta-5 acyl-CoA desaturase or fatty acyl-CoA elongase homologs, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *Proc. Natl. Acad. Sci. USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

Oil biosynthesis in plants has been fairly well-studied (see Harwood (1989) in Critical Reviews in Plant Sciences, Vol. 8:1–43). As used herein, "Oilseed crops" refers to plant species which produce and store triacylglycerol in specific organs, primarily in seeds. In particular, for purposes of this disclosure, "oilseed crops" refers to soybean, corn, sunflower, peanut, safflower, sesame, niger, cotton, cocoa, linseed (flax), low linoleic flax, castor, oil palm, coconut, canola and other Brassica oilseed species such as *B. napus, B. campestris, B. oleracea, B. carinata, B. juncea, B. nigra, B. adpressa, B. tournefortii, B. fruticulosas.*

The nucleic acid fragments of the instant invention may be used to create transgenic plants in which the disclosed delta-5 acyl-CoA desaturase or fatty acyl-CoA elongase are present at higher or lower levels than normal or in cell types or developmental stages in which they are not normally found. This would have the effect of altering the level of fatty acid saturation and chain length in those cells. As demonstrated in Example 6 below, overexpression of the Limnanthes fatty acyl-CoA elongase in an oilseed crop results in the elongation of palmitic acid (16:0) to arachidonic acid (20:0). Overexpression of the Limnanthes delta-5 acyl-CoA desaturase in an oilseed crop results in the introduction of a double bond at the delta-5 position of a fatty acid chain, resulting in the production of 16:1 and 18:1 delta-5 fatty acids. Overexpression of both of these genes in an oilseed crop will enable the production of 20:1 delta-5 fatty acids. There are at least two positive effects emanating from this: the reduction of the saturated fatty acids (especially 16:0) in food oils and the production of fatty acids (20:1 delta-5) with a myriad of industrial uses.

Overexpression of the delta-5 acyl-CoA desaturase or the fatty acyl-CoA elongase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant enzyme involved in lipid biosynthesis to different cellular compartments, or to facilitate its secretion from the cell. It is thus envisioned that the chimeric gene described above may be further supplemented by altering the coding sequence to encode delta-5 acyl-CoA desaturase or fatty acyl-CoA elongase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

The instant delta-5 acyl-CoA desaturase or fatty acyl-CoA elongase (or portions thereof) may be produced in heterologous host cells, particularly in the cells of microbial hosts, and can be used to prepare antibodies to the these proteins by methods well known to those skilled in the art. The antibodies are useful for detecting delta-5 acyl-CoA desaturase or fatty acyl-CoA elongase in situ in cells or in vitro in cell extracts. Preferred heterologous host cells for production of the instant delta-5 acyl-CoA desaturase or fatty acyl-CoA elongase are microbial hosts. Microbial expression systems and expression vectors containing regulatory sequences that direct high level expression of foreign proteins are well known to those skilled in the art. Any of these could be used to construct a chimeric gene for production of the instant delta-5 acyl-CoA desaturase or fatty acyl-CoA elongase. This chimeric gene could then be introduced into appropriate microorganisms via transformation to provide high level expression of the encoded enzyme involved in lipid biosynthesis. An example of a vector for high level expression of the instant delta-5 acyl-CoA desaturase or fatty acyl-CoA elongase in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1) :37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs *from Limnanthes douglasii* embryo tissues were prepared in pcDNAII vectors according to the manufacturer's protocol (Invitrogen Corporation, Carlsbad, Calif.). cDNA inserts from randomly picked bacterial colonies containing recombinant pcDNAII plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding enzymes involved in lipid biosynthesis were identified by conducting BLAST (Basic Local Alignment Search Tool; Altschul, S. F., et al., (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Delta-5 Acyl-CoA Desaturase Homologs The BLASTX search using the EST sequences from clones lde.pk0004.c10, lde.pk0012.e5 and lde.pk0012.g11, and the entire cDNA insert from clone lde.pk00108.a8 revealed similarity of the proteins encoded by the cDNAs to delta-9 acyl-lipid desaturase/delta-9 acyl-CoA desaturase from *Rosa hybrida* (GenBank Accession No. S80863; NCBI General Identifier No. 1911477). The BLASTX search using the EST sequence from clone lde.pk0008.b9 revealed similarity of the protein encoded by the cDNA to a fatty-acid desaturase from *Rosa hybrida* (GenBank Accession No. D49383; NCBI General Identifier No. 2580425) The BLAST results for each of these sequences are shown in Table 2:

TABLE 2

BLAST Results for Clones Encoding Polypeptides Homologous to Desaturases

| Clone | GenBank Accession No. | BLAST pLog Score |
|---|---|---|
| lde.pk0004.c10 | S80863 | 48.23 |
| lde.pk0012.e5 | S80863 | 23.64 |
| lde.pk0012.g11 | S80863 | 14.42 |
| lde.pk0010.a8 | S80863 | 9.89 |
| lde.pk0008.b9 | D49383 | 1.44 |

The sequence of the entire cDNA insert in clone lde.pk0008.b9 was determined and is shown in SEQ ID NO:1; the deduced amino acid sequence of this CDNA is shown in SEQ ID NO:2. The EST sequences for clones lde.pk0004.c10, lde.pk0012.e5, lde.pk0012.g11 and lde.pk0010.a8 are encompassed by the sequence set forth in SEQ ID NO:1. The amino acid sequence set forth in SEQ ID NO:2 was evaluated by BLASTP, yielding a pLog value of >250 versus the *Arabidopsis thaliana* delta-9 desaturase sequence (NCBI General Identifier No. 2970034). FIG. 1 presents an alignment of the amino acid sequences set forth in SEQ ID NO:2 and the *Arabidopsis thaliana* delta-9 desaturase sequence (SEQ ID NO:3). The amino acid sequence set forth in SEQ ID NO:2 is 47.9% similar to the *Arabidopsis thaliana* sequence (SEQ ID NO:3). Sequence alignments and percent identity calculations were performed using the Megalign program of the LASARGENE bioinformatics computing suite (DNASTAR Inc., Madison, Wis.). Pairwise alignment of the amino acid sequences and percent similarity calculations were performed using the Clustal method of alignment (Higgins, D. G. and Sharp, P. M. (1989) *CABIOS*. 5: 151–153) with the default parameters (GAP PENALTY=5, KTUPLE=1, WINDOW=5 and DIAGONALS SAVED=5).

Sequence alignments, BLAST scores and probabilities suggested that the instant nucleic acid fragment encodes an entire Limnanthes delta-9 acyl-CoA desaturase. However, the oil derived from Limnanthes is composed mainly of very long-chain fatty acids with a delta-5 cis double bond, suggesting that the instant nucleic acid fragment may in fact encode a delta-5 acyl-CoA desaturase rather than a delta-9 desaturase. As shown in Example 6, expression of the Limnanthes desaturase in soybean embryos results in the formation of oils containing 16:1 and 18:1 delta-5 fatty acids. Accordingly, the instant nucleic acid fragments comprise the first Limnanthes douglasii sequences encoding a delta-5 acyl-CoA desaturase.

Example 4

Characterization of cDNAs Clones Encoding Fatty Acyl-CoA Elongase Homologs

The BLASTX search using the EST sequences from clones lde.pk0008.d5 and lde.pk0010.e4 revealed similarity of the proteins encoded by the cDNAs to beta-ketoacyl-CoA synthase from *Arabidopsis thaliana* (GenBank Accession No. AC003105; NCBI General Identifier No. 2760830). The BLAST results for these ESTs are shown in Table 3:

TABLE 3

BLAST Results for a Clone Encoding a Polypeptide Homologous to Beta-ketoacyl-CoA Synthase

| Clone | BLAST pLog Score AC003105 |
| --- | --- |
| lde.pk0008.d5 | 78.05 |
| lde.pk0010.e4 | 72.66 |

Further searching of the proprietary database indicated that clone lde.pk0015.d10 also revealed similarity to beta-ketoacyl-CoA synthase. The sequence of the entire cDNA insert in clone lde.pk0008.d5 was determined and a contig was assembled with this sequence and the sequence from a portion of the cDNA insert from clone lde.pk0015.d10. The nucleotide sequence of this contig is shown in SEQ ID NO:4; the deduced amino acid sequence of this contig is shown in SEQ ID NO:5. A BLASTX search using the nucleotide sequence set forth in SEQ ID NO:4 resulted in a pLog value of >254 versus the *Arabidopsis thaliana* beta-ketoacyl-CoA synthase sequence. The sequence of almost the entire cDNA insert from clone lde.pk0010.e4 is shown in SEQ ID NO:6; the deduced amino acid sequence of this cDNA is shown in SEQ ID NO:7. A BLASTX search using the nucleotide sequences set forth in SEQ ID NO:6 resulted in a pLog value of 132 versus the *Arabidopsis thaliana* sequence. The amino acid sequence set forth in SEQ ID NO:5 is 74.5% similar to the *Arabidopsis thaliana* sequence and the amino acid sequence set forth in SEQ ID NO:7 is 80.3% similar to the *Arabidopsis thaliana* sequence. The two Limnanthes sequences are 88.0% similar to each other, suggesting that both Limnanthes sequences encode proteins of similar function.

BLAST scores and probabilities indicated that the instant nucleic acid fragments encoded a portion of a *Limnanthes douglasii* beta-ketoacyl-CoA synthase homolog and an entire *Limnanthes douglasii* beta-ketoacyl-CoA synthase homolog. However, the oil in Limnanthes is composed mainly of very long-chain fatty acids with a delta-5 cis double bond suggesting that the instant nucleic acid fragments may in fact encode fatty acyl-CoA elongases rather than beta-ketoacyl-CoA synthases. This is confirmed in Example 6 wherein expression of the Limnanthes elongase in soybean embryos results in an enrichment of 20:0 fatty acids. These sequences therefore represent the first *Lumnanthes douglasii* sequences encoding fatty acyl-CoA elongases.

Example 5

Expression of Chimeric Genes in Monocot Cells

A chimeric gene comprising a cDNA encoding an enzyme involved in lipid biosynthesis in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding an enzyme involved in lipid biosynthesis, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein T M et al. (1987) *Nature* (London) 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Biol/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle, J. J. et al. (1986) *J. Biol. Chem.* 261:9228–9238) can be used for expression of the instant enzymes involved in lipid biosynthesis in transformed dicots. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Dicot embroys may then be transformed with the expression vector comprising sequences encoding enzymes involved in lipid biosynthesis. To induce somatic embryos, cotyledons, 3–5 mm in length dissected from surface sterilized, immature seeds of the chosen dicot, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Dicot embryogenic suspension cultures can maintained in 35 mL liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Dicot embryogenic suspension cultures may then be transformed by the method of particle gun bombardment (Klein T. M. et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate plant transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz L et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the enzyme involved in lipid biosynthesis and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment replaced with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Expression of Limnanthes Delta-5 Acyl-CoA Desaturase and Fatty Acyl-CoA Elongase in Soybean Embryos To confirm the identity and activity of the nucleic acid fragments set forth in SEQ ID NO:1 (encoding a Limnanthes delta-5 acyl-CoA lipid desaturase) and SEQ ID NO:4 (encoding a Limnanthes fatty acyl-CoA elongase), these nucleic acids were cloned individually into an in vivo expression vector. The cDNA inserts in the library cloning vector pcDNAII are flanked by Not I sites allowing for the removal of the entire cDNA insert by Not I digestion. The delta-5 acyl-CoA desaturase and the fatty acyl-CoA elongase-encoding plasmids were digested with Not I, the cDNA fragment isolated, purified and ligated into the pKS67 vector (described below) following standard molecular biology techniques.

A plasmid, pZBL100, containing chimeric genes to allow expression of hygromycin B phosphotransferase in certain bacteria and in plant cells was constructed from the following genetic elements: a) T7 promoter+Shine-Delgarno/hygromycin B phosphotransferase (HPT)/T7 terminator sequence, b) 35S promoter from cauliflower mosaic virus (CaMV)/hygromycin B phosphotransferase (HPT)/nopaline synthase (NOS3' from *Agrobacterium tumefaciens* T-DNA, and c) pSP72 plasmid vector (Promega) with the b-lactamase coding region (ampicillin resistance gene) removed.

The HPT gene was amplified by PCR from *E. coli* strain W677, which contained a Klebsiella-derived plasmid pJR225. Starting with the pSP72 vector the elements were assembled into a single plasmid using standard cloning methods (Maniatis).

Plasmid pZBL100 thus contains the T7 promoter/HPT/T7 terminator cassette for expression of the HPT enzyme in certain strains of *E. coli*, such as NovaBlue (DE3) (Novagen), that are lysogenic for lambda DE3 (which carries the T7 RNA Polymerase gene under lacUV5 control). Plasmid pZBL100 also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pZBL 100 also contains three unique restriction endonuclease sites suitable for the cloning of other chimeric genes into this vector.

Plasmid pCW109 was derived from the commercially available plasmid pUC18 (Gibco-BRL) by inserting into the Hind III site of the cloning vector pUC18 a 555 bp 5' non-coding region (containing the promoter region) of the b-conglycinin gene followed by the multiple cloning sequence containing the restriction endonuclease sites for Nco I, Sma I, Kpn I and Xba I, then 1174 bp of the common bean phaseolin 3' untranslated region into the Hind III site. The b-conglycinin promoter region used is an allele of the published b-conglycinin gene (Doyle et al. (1986) *J. Biol. Chem.* 261:9228–9238) due to differences at 27 nucleotide positions. A unique Not I site was introduced into the cloning region between the -conglycinin promoter and the phaseolin 3' end in pCW109 by digestion with Nco I and Xba I followed by removal of the single stranded DNA ends with mung bean exonuclease. Not I linkers (New England Biochemical catalog number NEB 1125) were ligated into the linearized plasmid to produce plasmid pAW35.

Plasmid pML 18 consists of the non-tissue specific and constitutive cauliflower mosaic virus (35S) promoter (Odell, J. T. et al. (1985) *Nature* 313:810–812; Hull et al. (1987) *Virology* 86:482–493), driving expression of the neomycin phosphotransferase gene described in (Beck, E. et al. (1982) *Gene* 19:327–336) followed by the 3' end of the nopaline synthase gene including nucleotides 848 to 1550 described by (Depicker et al. (1982) *J. Appl. Genet.* 1:561–574). This transcriptional unit was inserted into the commercial cloning vector pGEM9Z (Gibco-BRL) and is flanked at the 5' end of the 35S promoter by the restriction sites Sal I, Xba I, Bam HI and Sma I in that order. An additional Sal I site is present at the 3' end of the NOS 3' sequence and the Xba I, Bam HI and Sal I sites are unique. The single Not I site in pML 18 was destroyed by digestion with Not I, filling in the single stranded ends with dNTPs and Klenow fragment followed by re-ligation of the linearized plasmid. The modified pML 18 was then digested with Hind III and treated with calf intestinal phosphatase. The b-conglycinin:Not I:phaseolin expression cassette in pAW35 was removed by digestion with Hind III and the 1.8 kB fragment was isolated by agarose gel electrophoresis and ligated into the modified and linearized pML 18 construction an described above. A clone with the desired orientation was identified by digestion with Not I and Xba I to release a 1.08 kB fragment indicating that the orientation of the -conglycinin transcription unit was the same as the selectable marker transcription unit. The resulting plasmid was given the name pBS 19.

The pKS67 vector was prepared by isolating the b-conglycinin-containing fragment from pBS19 by digestion with Hind III, isolation by gel electrophoresis and ligation into the Hind III-digested pZBL100, which had been treated with calf alkaline phosphatase.

Soybean embryogenic suspension cultures were transformed with the expression vectors by the method of particle gun bombardment (Klein, T. M. et al. (1987) *Nature* (London) 327:70–73, U.S. Pat. No. 4,945,050). Maintenance of transgenic embryos, preparation of oils, and measurement of the fatty acid content by gas chromatography was performed as indicated in PCT publication WO93/11245 (incorporated herein by reference).

Demonstration of Elongase Activity

Figure 3A:
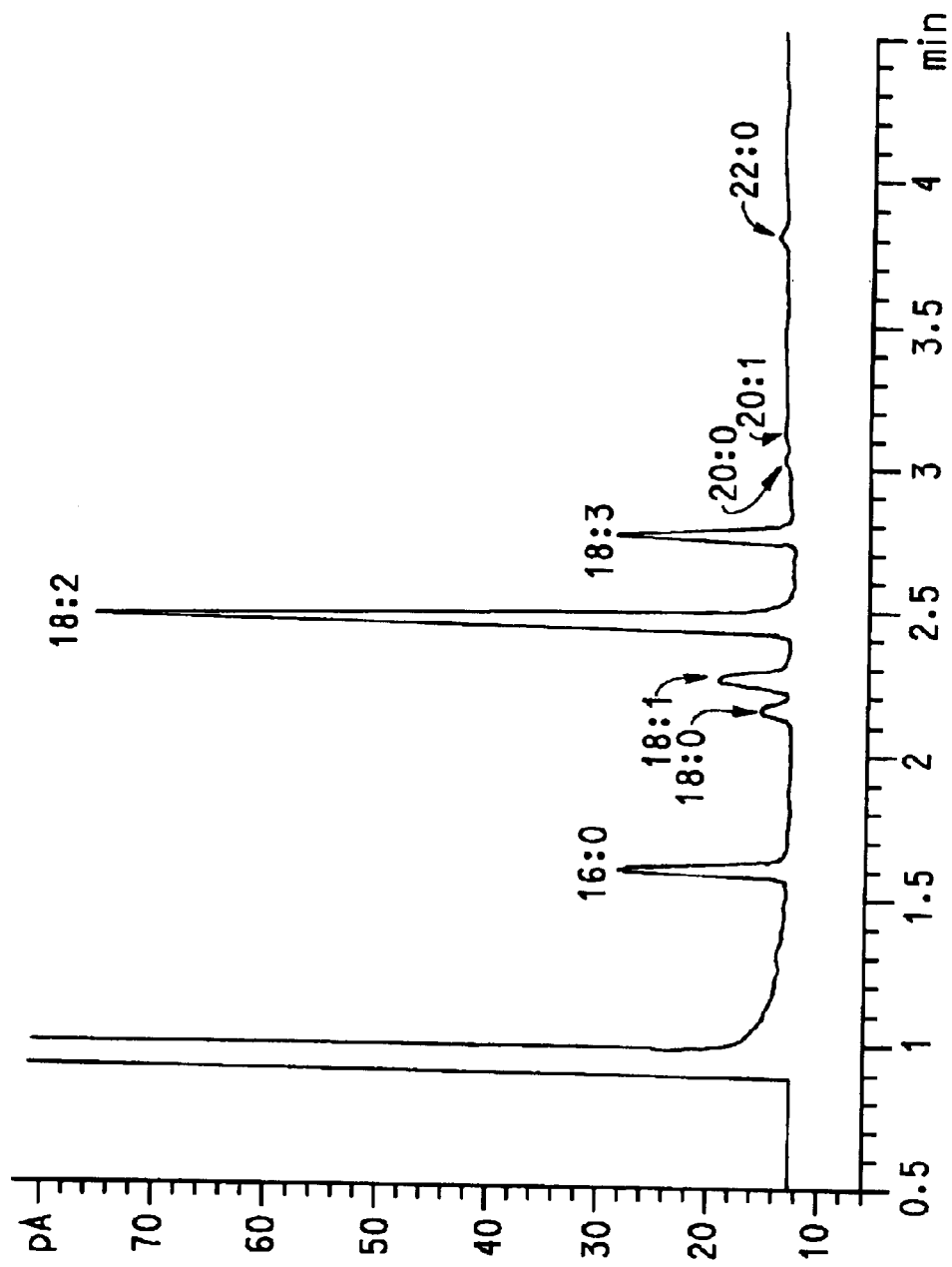
FIG. 3 shows the tracings from gas chromatograms obtained for the oils of wild type soybean embryos (FIG. 3(A)) and of soybean embryos expressing the Limnanthes fatty acyl-CoA elongase (FIG. 3(B), demonstrating the production of C20 fatty acids in the transformed soybean embryos. The fatty acids corresponding to the various peaks of the chromatogram are indicated.
Figure 3B:
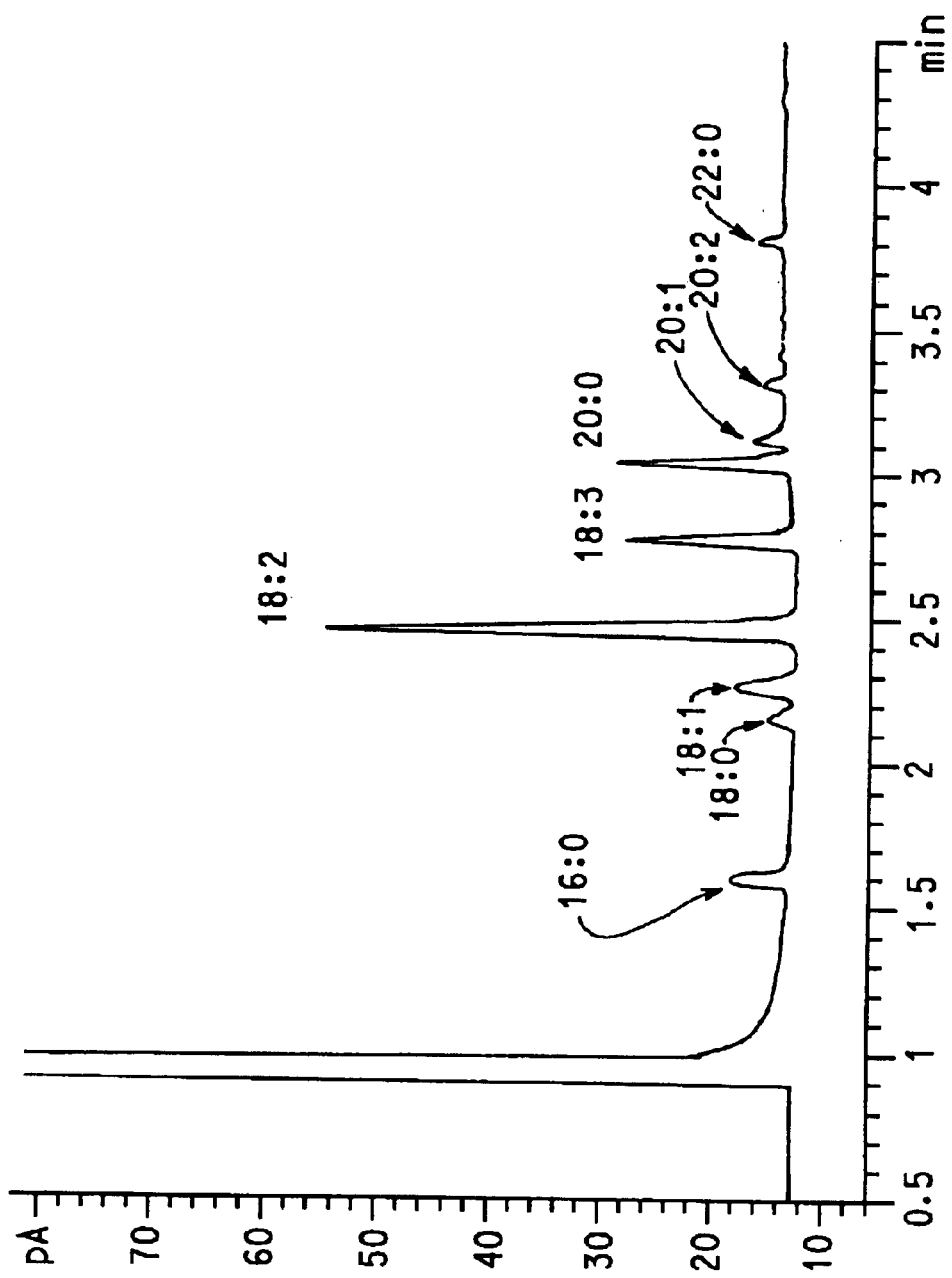

The percent accumulation of 16:0 fatty acids decreases in soybean embryos expressing the fatty acyl-CoA elongase while the levels of 20:0 fatty acids dramatically increase. FIG. 3 presents a chromatographic analysis of oils derived wild-type, non-transgenic soybean embryos (FIG. 3(A)) and from transgenic soybean embryos expressing the Limnanthes fatty acyl-CoA elongase (FIG. 3(B)). The peaks corresponding to the different fatty acids present in the oils are indicated. The quantity of 16:0 and 18:2 fatty acids are decreased in the oils from the fatty acyl-CoA elongase-expressing soybean embryos when compared to oil derived wild-type, non-transgenic soybean embryos. In addition, the quantity of 20:0 fatty acids is greatly enriched in the oils of the transgenic embryos. The quantified distribution of 16:0 and 20:0 fatty acids in wild-type soybean embryos and in soybean embryos expressing the Limnanthes fatty acyl-CoA elongase is shown in Table 4. The levels of 20:0 fatty acids in wild type embryos range from 0.2 to 0.6% whereas in fatty acyl-CoA elongase-expressing embryos, the percent of 20:0 fatty acids ranges from 7.7% to 11.0%.

TABLE 4

Percent Fatty Acid Distribution in Transgenic Soybean Embryos Expressing Limnanthes Fatty Acyl-CoA Elongase

| Embryo | 16:0 | 20:0 |
|---|---|---|
| 4155 (wild-type) | 12.9 | 0.2 |
| 323 (wild-type) | 13.0 | 0.4 |
| 312 (wild-type) | 18.4 | 0.6 |
| 4111 (wild-type) | 15.4 | 0.6 |
| 4102 (wild-type) | 15.2 | 0.6 |
| 195 (wild-type) | 16.2 | 0.6 |
| 155 (transgenic) | 7.4 | 9.3 |
| 161 (transgenic) | 7.6 | 8.2 |
| 163 (transgenic) | 7.9 | 7.7 |
| 175 (transgenic) | 8.4 | 11.0 |
| 2211 (transgenic) | 8.5 | 7.9 |
| 341 (transgenic) | 6.4 | 10.8 |

Figure 4:
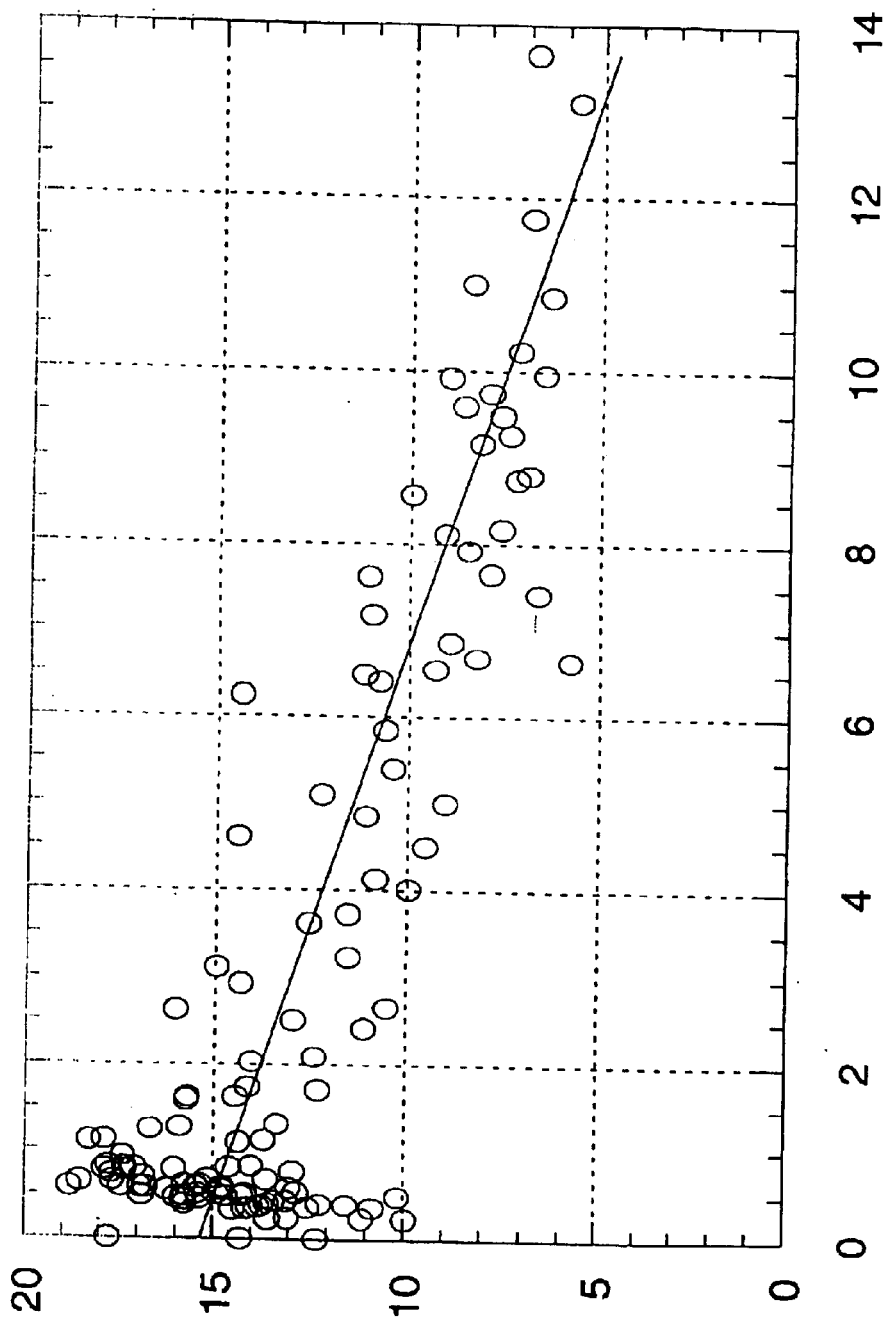
FIG. 4 shows the decrease in 16:0 fatty acid accumulation concomitant with the increase in 20:0 fatty acids in individual transgenic soybean embryos expressing the Limnanthes fatty acyl-CoA elongase.

FIG. 4 depicts the linear relationship between the decrease in 16:0 fatty acid content and the increase in 20:0 fatty acid content in transgenic soybean embryos expression the Limnanthes fatty acyl-CoA elongase.

Demonstration of Delta-5 Desaturase Activity

Figure 5A:
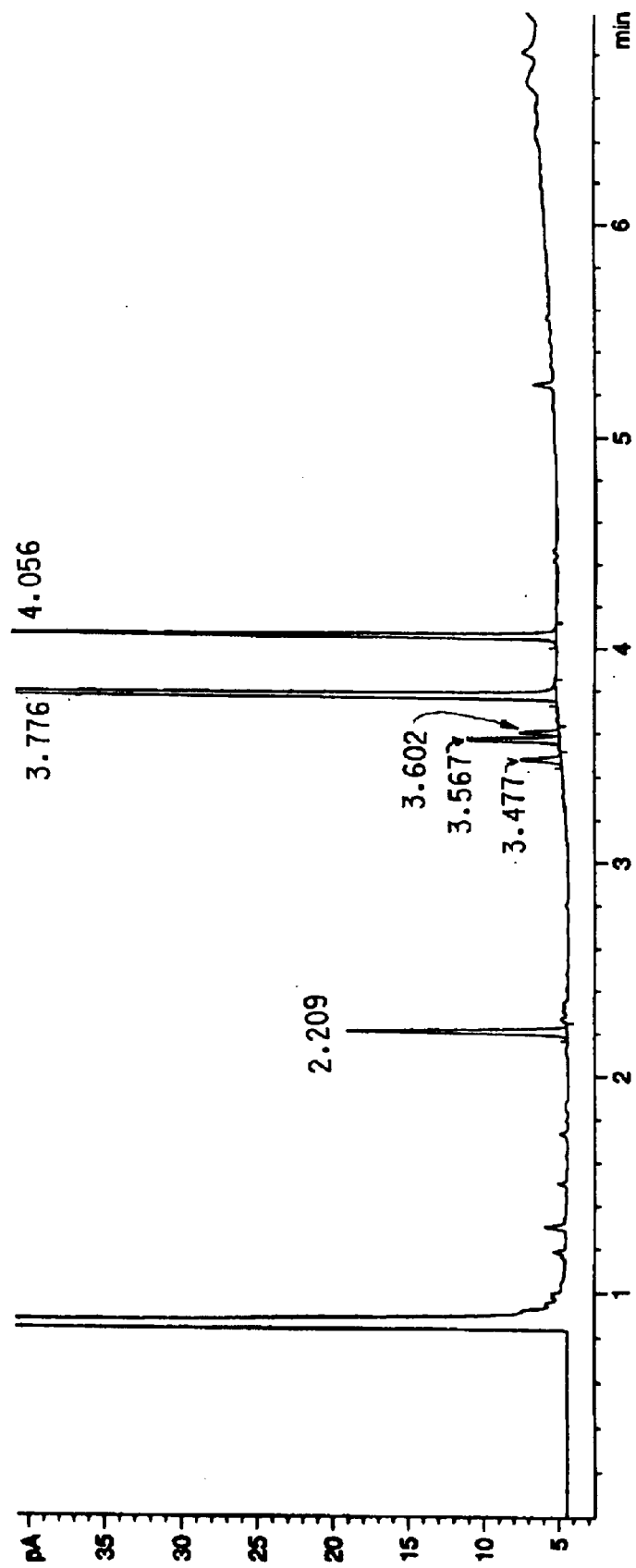
FIG. 5 shows the tracings from gas chromatograms obtained for the oils of wild type soybean embryos (FIG. 5(A)) and of soybean embryos expressing the Limnanthes delta-5 acyl-CoA desaturase (FIG. 5(B)). The relevant fatty acids are indicated by their retention time: 2.209 is 16:0; 2.271 is 16:1Δ5; 3.477 is 18:0; 3.530 is 18:1Δ5; and 3.567 is 18:1Δ9.
Figure 5B:
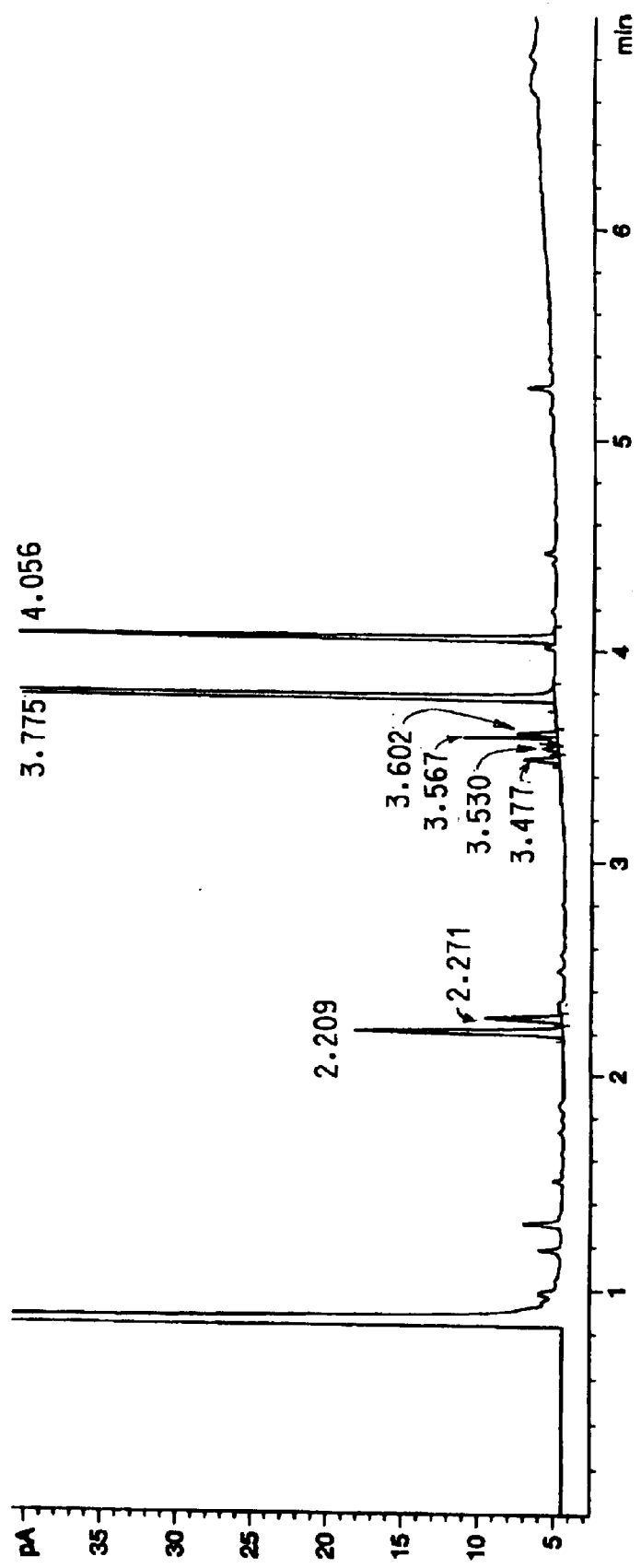

Transgenic soybean embryos expressing the Limnanthes delta-5 acyl-CoA desaturase produce 16:1 fatty acids not seen in wild type embryos. The fatty acid distribution in soybean embryos expressing the delta-5 desaturase is illustrated in FIG. 5 which shows the chromatograms corresponding to oils derived from wild type soybean embryos (FIG. 5(A)) and soybean embryos expressing the Limnanthes delta-5 acyl-CoA desaturase (FIG. 5(B)). Table 5 shows the quantified percent distribution of 16:0, 16:1 delta-5, 18:0 and 18:1 delta-5 in wild-type embryos and transgenic embryos expressing the Limnanthes delta-5 acyl-CoA desaturase:

TABLE 5

Percent Fatty Acid Distribution in Transgenic Soybean Embryos Expressing Limnanthes Delta-5 Acyl-CoA Desaturase

| Embryo | 16:0 | 16:1Δ5 | 18:0 | 18:1Δ5 |
|---|---|---|---|---|
| 216.0 (wild-type) | 13.03052 | 0 | 2.47064 | 0 |
| 216.1 (wild-type) | 10.60185 | 0 | 1.76857 | 0 |
| 216.2 (wild-type) | 11.95366 | 0 | 1.67544 | 0 |
| 218.0 (wild-type) | 12.93328 | 0 | 2.15752 | 0 |
| 218.5 (wild-type) | 11.57688 | 0 | 2.24243 | 0 |
| 220.0 (transgenic) | 10.17740 | 3.63283 | 1.25350 | 0.57574 |
| 220.1 (transgenic) | 8.99496 | 4.27946 | 1.22194 | 0.71544 |
| 220.2 (transgenic) | 9.78203 | 2.86631 | 1.57083 | nd |
| 220.3 (transgenic) | 9.47315 | 3.35682 | 1.49796 | 0.60828 |
| 220.4 (transgenic) | 12.16690 | 2.46238 | 1.84877 | 0.45737 |
| 220.5 (transgenic) | 12.22757 | 2.75365 | 2.38873 | 0.53878 |
| 220.6 (transgenic) | 11.72778 | 2.43411 | 2.37860 | 0.57778 |
| 220.7 (transgenic) | 9.31376 | 3.39302 | 1.33830 | 0.59855 |
| 220.8 (transgenic) | 9.48067 | 3.66554 | 1.45045 | 0.66508 |
| 220.9 (transgenic) | 9.37735 | 3.47590 | 0.95774 | 0.75598 |
| 217.1 (transgenic) | 9.86364 | 3.56592 | 1.51745 | 0.64637 |
| 217.2 (transgenic) | 11.03674 | 2.79068 | 1.92739 | 0.55140 |
| 217.3 (transgenic) | 13.57543 | 2.45928 | 2.26611 | 0.56306 |
| 217.4 (transgenic) | 11.33959 | 2.88931 | 1.73524 | 0.53747 |
| 217.5 (transgenic) | 9.61358 | 3.40842 | 1.94986 | 0.73811 |
| 217.6 (transgenic) | 10.54626 | 3.11490 | 1.69327 | nd |
| 217.7 (transgenic) | 11.60064 | 3.34681 | 2.77254 | 0.78978 |
| 217.5 (transgenic) | 13.76804 | 1.41011 | 3.41123 | nd |
| 217.9 (transgenic) | 11.21888 | 2.98101 | 1.87345 | 0.61650 | nd = not enough 18:1 delta-5 produced to be integrated by the instrument.

To confirm the location of the double bond catalyzed by the desaturase, double bond positions of monounsaturated fatty acids were established by GC-MS analysis of disulfide derivatives of fatty acid methyl esters as described by Yamamoto, K. et al. (1991) *Chem Phys Lipids* 60:39–50 and illustrated in FIG. 6.

Fatty acid methyl esters prepared from soybean embryos expressing the Limnanthes delta-5 acyl-CoA desaturase were reacted with dimethyl disulfide as previously described (Yamamoto, K. et al. (1991) *Chem. Phys. Lipids* 60:39–50). This reaction converts the double bonds of unsaturated fatty acid methyl esters to dimethyl disulfide (DMDS) adducts. When analyzed by GC-MS, these derivatives yield ions that are diagnostic for the positions of double bonds in fatty acids. The DMDS derivatives of fatty acid methyl esters from the transgenic soybean embryos were analyzed by GC-MS. These derivatives were resolved using a 0.25 mm (inner diameter)×30 m HP-INNOWax column (Hewlett Packard) with the oven temperature of an HP6890 gas chromatograph temperature programmed from 185° C. (5 min hold) to 237° C. (25 min hold) at a rate of 7.5° C./min. The mass spectrum of the resolved DMDS derivatives was obtained using an HP5973 mass selective detector that was interfaced with the gas chromatograph. DMDS derivatives of methyl hexadecenoic acid (16:1) were identified using a selected ion scan for 362 m/z, which corresponds to the molecular ion of the DMDS derivatives of methyl 16:1. This resulted in the identification of two peaks with retention times between 18.5 and 19.5 minutes (FIG. 6(A)). The mass spectrum of the largest of these peaks contained abundant ions with m/z of 161 and 201 (FIG. 6(B)). The masses of these ions are consistent with the presence of the double bond at the delta-5 carbon atom. The 161 m/z ion (Fragment Y) is the expected mass for the carboxyl portion of the methyl 16:1Δ5 DMDS derivative and the 201 m/z ion (Fragment X) is the expected mass for the methyl end of the 16:1Δ5 DMDS derivative. Also consistent with the identification of this peak as 16:1Δ5 DMDS derivative is the 129 m/z ion which is generated by rearrangement of Fragment Y with the loss of 32 m/z. In general, the Y-32 ion is considered a diagnostic ion for DMDS derivatives of methyl esters of monounsaturated fatty acids (Francis, G. W. (1981) *Chem. Phys. Lipids* 29:369–374). Of note, the second and smaller peak in FIG. 6(A) was identified as the DMDS derivative of methyl 16:1Δ9 (results not shown). This fatty acid, in contrast to 16:1Δ5, is detectable in small amounts in virtually all plant tissues.

Figure 6A:
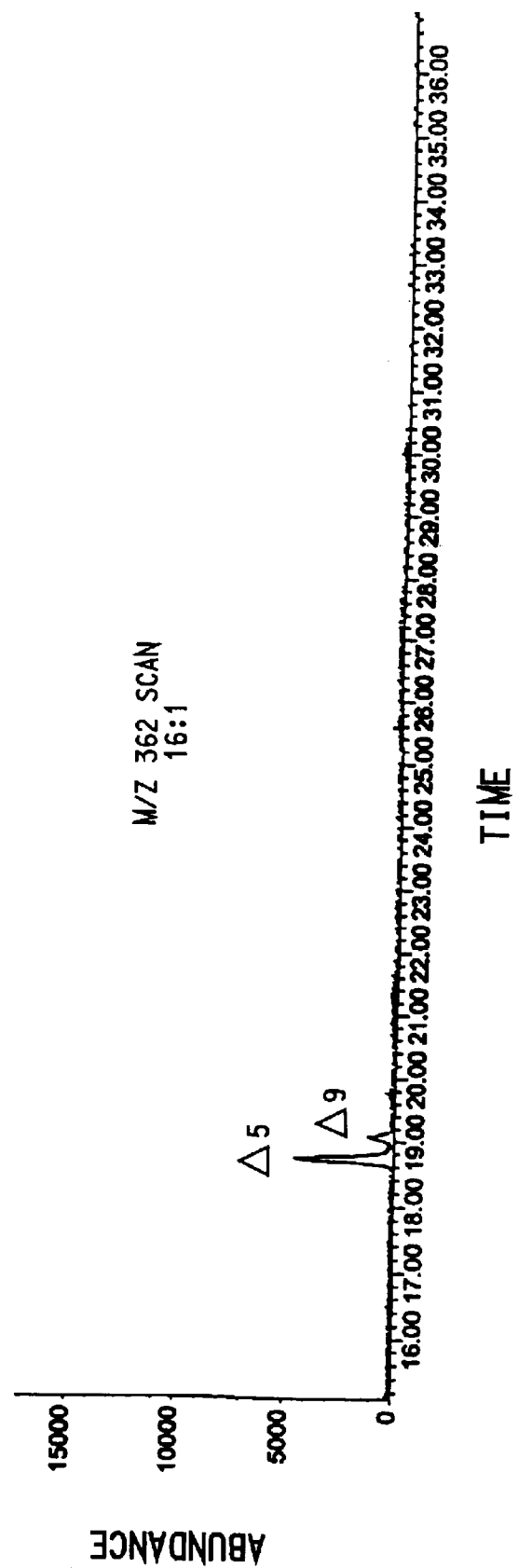
Figure 6B:
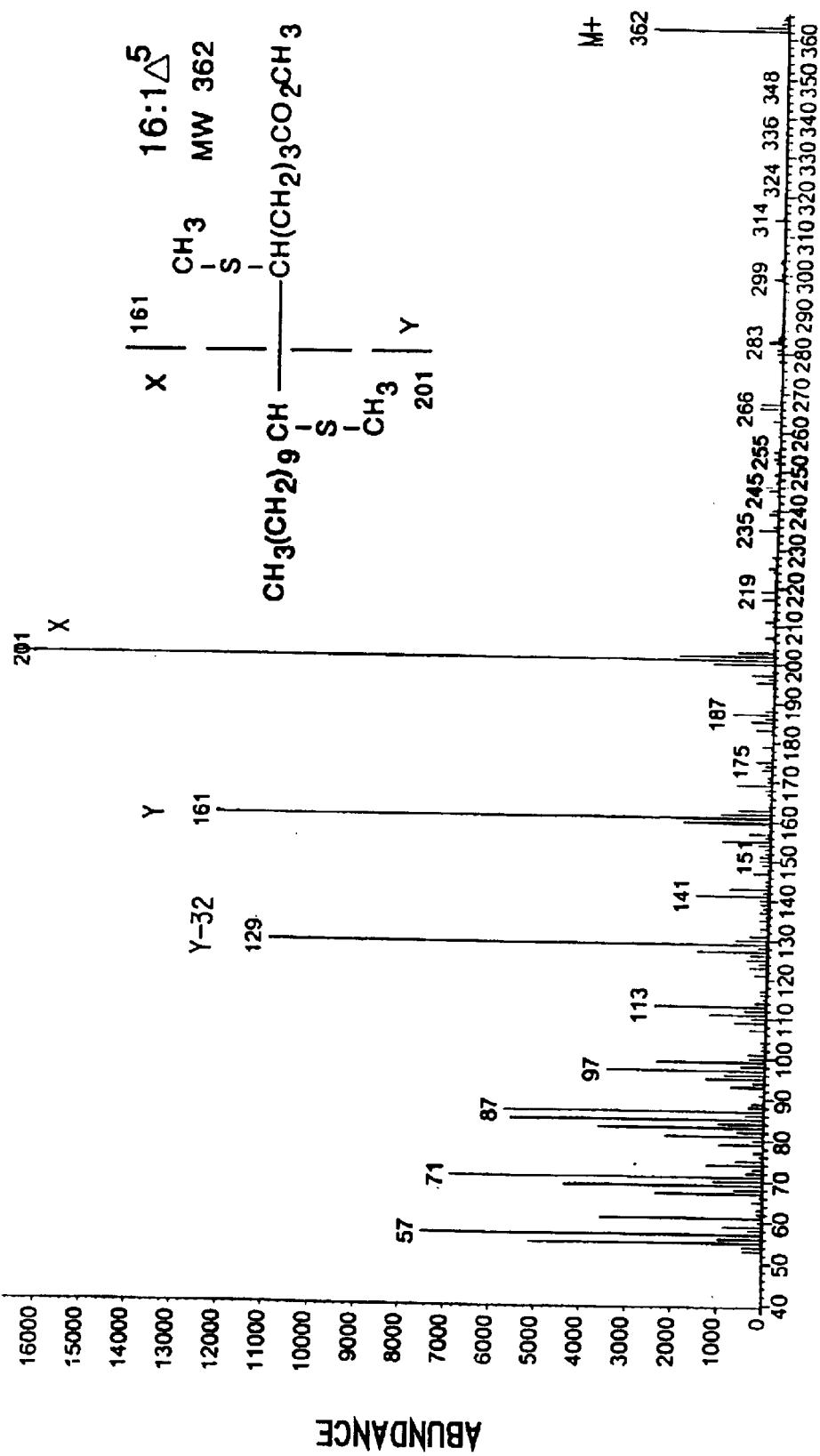
Figure 6C:
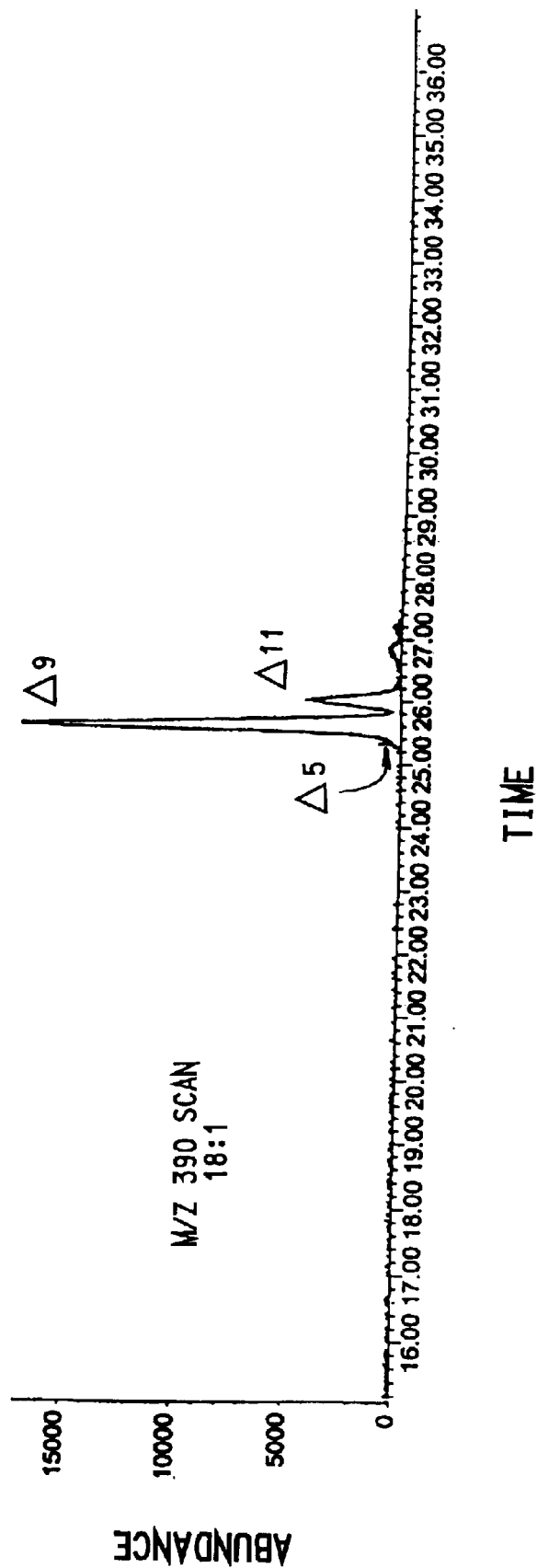
Figure 6D:
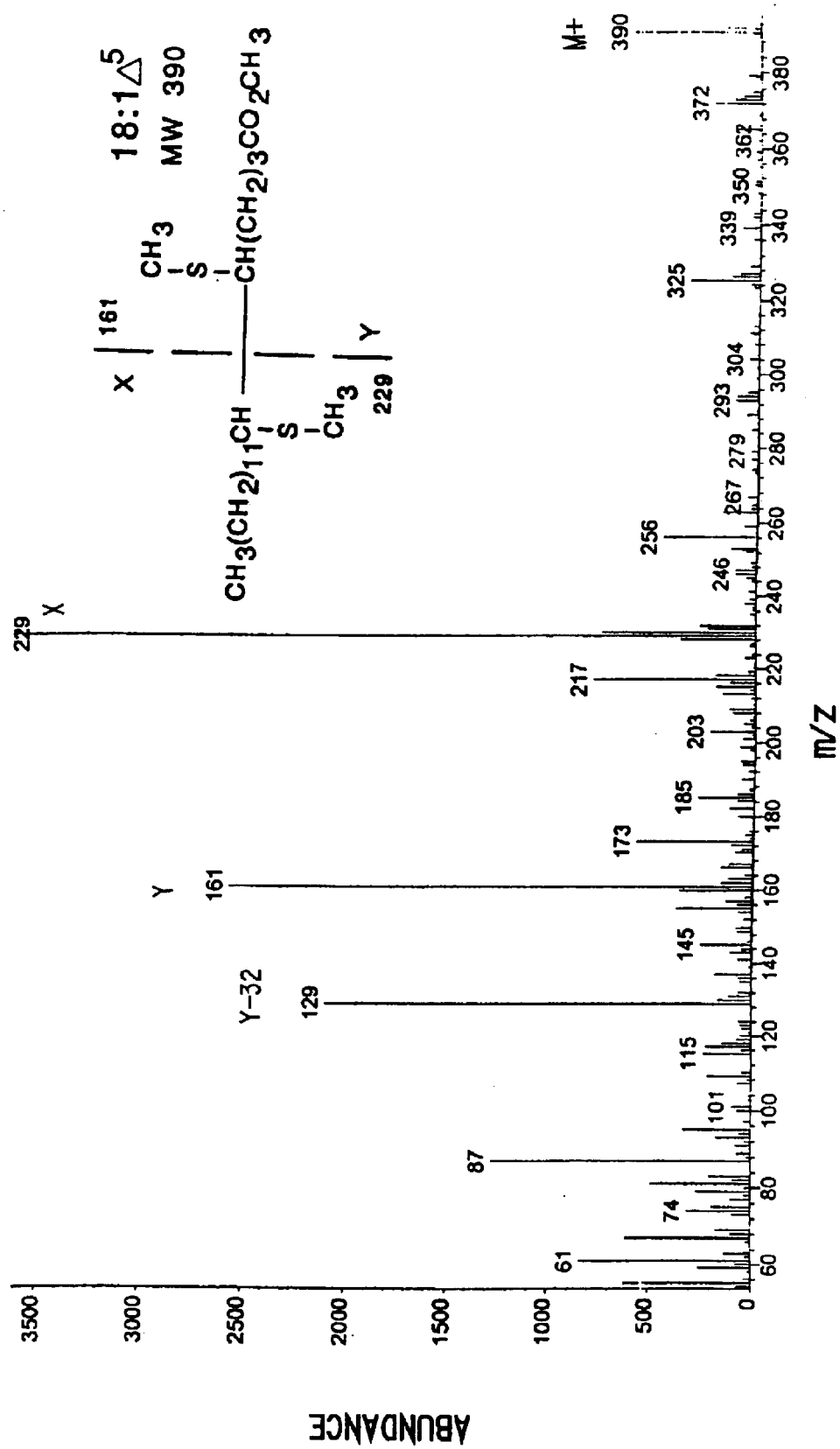

Methyl octadecenoic acid (18:1) DMDS derivatives were initially identified using a selected ion scan for 390 m/z (FIG. 6(C)), that corresponds to the mass of the molecular ion of these adducts. As shown in FIG. 6(D), the fragmentation of the DMDS derivative of methyl 18:1Δ5 would be expected to generate ions of 161 m/z, 229 m/z, and 129 m/z that correspond to Fragments Y, X, and Y-32, respectively. These ions were detected in a shoulder on the front of the peak corresponding to the derivative of methyl 18:1Δ9, the major monounsaturated fatty acid of soybean embryos.

The results presented herein establish the occurrence of 16:1Δ5 and 18:1Δ5 in fatty acid methyl esters derived from transgenic soybean embryos expressing the Limnanthes delta-5 acyl-CoA desaturase. Neither fatty acid was detectable in derivatives prepared from wild-type soybean embryos.

These experiments show that when expressed in soybean embryos, the Limnanthes fatty acyl-CoA elongase (SEQ ID NO:5) catalyzes the production of arachidonate (20:0) from palmitate (16:0). These experiments also show that the Limnanthes acyl-CoA desaturase (SEQ ID NO:2) encodes a delta-5 desaturase which produces 16:1 delta-5 and 18:1 delta-5 fatty acids when expressed in transgenic soybean embryos. These experiments are the first demonstration of the activity of the *Limnanthes douglasii* delta-5 acyl-CoA desaturase and the fatty acyl-CoA elongase whose sequences are set forth in SEQ ID NO:2, SEQ ID NO:5 and SEQ ID NO:7.

Expression of the Limnanthes fatty acyl-CoA elongase in other oil producing crops will increase the amounts of C20:0 from about less than 1% to over about 15%. Expression of the Limnanthes fatty acyl-CoA elongase and delta-5 acyl-CoA desaturase in other oil seed crops will have the result of producing 20:1 delta-5 oils which may then be used in the production of industrially-useful compounds.

Example 7

Expression of Chimeric Genes in Microbial Cells

The cDNAs encoding the instant enzyme involved in lipid biosynthesis can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the enzyme involved in lipid biosynthesis are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having delta-5 acyl-CoA desaturase activity, wherein the polypeptide has an amino acid sequence of SEQ ID NO:2, or
   (b) the full complement of the nucleotide sequence.

2. A vector comprising the polynucleotide of claim 1.

3. A method for transforming a cell comprising transforming a cell with the polynucleotide of claim 1.

4. A method for producing a plant comprising transforming a plant cell with the polynucleotide of claim 1 and regenerating a plant from the transformed plant cell.

5. A plant comprising the chimeric gene of claim 1.

6. A seed comprising the chimeric gene of claim 1.

7. A method for isolating a polypeptide encoded by the polynucleotide of claim 1 comprising isolating the polypeptide from a cell containing a chimeric gene comprising the polynucleotide operably linked to a regulatory sequence.

8. The isolated polynucleotide of claim 1 wherein the nucleotide sequence comprises SEQ ID NO:1.

9. A chimeric gene comprising the nucleic acid fragment of claim 1 operably linked to a regulatory sequence.

10. A transformed host cell comprising the chimeric gene of claim 9.

11. A method of altering the level of expression of a delta-5 acyl-CoA desaturase in a host cell comprising:
    (a) transforming a host cell with the chimeric gene of claim 9; and
    (b) growing the transformed host cell produced in step (a) under conditions that are suitable for expression of the chimeric gene
   wherein expression of the chimeric gene results in production of altered levels of a delta-5 acyl-CoA desaturase in the transformed host cell.

12. A method of producing a desaturated fatty acid comprising a double bond in the delta-5 position in a host cell, the method comprising:
    (a) transforming a host cell with the chimeric gene of claim 9; and
    (b) growing the transformed host cell produced in step (a) under conditions that are suitable for expression of the chimeric gene
   wherein expression of the chimeric gene results in production of a desaturated fatty acid comprising a double bond in the delta-5 position.

13. A method of producing seed oil comprising a desaturated fatty acid wherein the fatty acid comprises a double bond in the delta-5 position, the method comprising:
    (a) transforming a plant cell with the chimeric gene of claim 9;
    (b) growing a fertile plant from the transformed plant cell of step (a);
    (c) obtaining a seed from the plant of step (b); and
    (d) processing the seed of step (c) to obtain oil
   wherein the oil comprises a desaturated fatty acid wherein the fatty acid comprises a double bond in the delta-5 position.

14. The method of claim 13 wherein the plant cell is derived from an oilseed crop.

15. The method of claim 14 wherein the oilseed crop is soybean.

* * * * *

UNITED STATES PATENT AND TRADEMARK OFFICE
CERTIFICATE OF CORRECTION

PATENT NO. : 6,838,594 B1  Page 1 of 1
APPLICATION NO. : 09/664840
DATED : January 4, 2005
INVENTOR(S) : Anthony J. Kinney and Steven J. Vollmer It is certified that error appears in the above-identified patent and that said Letters Patent is hereby corrected as shown below:

Col. 37 line 23, Claim No. 5: delete "claim 1" and insert therefor --claim 9--.

Col. 37 line 24, Claim No. 6: delete "claim 1" and insert therefor --claim 9--.

Signed and Sealed this

Twelfth Day of December, 2006

JON W. DUDAS
*Director of the United States Patent and Trademark Office*

SEQUENCE LISTING

```
<160> NUMBER OF SEQ ID NOS:  7

<210> SEQ ID NO 1
<211> LENGTH: 1355
<212> TYPE: DNA
<213> ORGANISM: Limnanthes douglasii

<400> SEQUENCE: 1
```

```
gcttgagact ctctctctac ttccccatct ctatatctct ctctctctct ctagaagcca      60
tggcttcttt catcgcaacc acaacaccag caatgccagc tttcgcttca gttcttgatc     120
caaaaatacc cacaaaacca gaacccaaaa ccgaaacccc caaaccaaaa gacgatctcg     180
aacgcttccg gacatcagaa gtcgtgttgg agaggaaatc caaggattc tggcgccgga      240
aatggaaccc tcgtgatatt caaaacgccg tcactttact ggtcctgcat gctcttgcag     300
cgatggcgcc cttttatttc agctgggatg cgttttggat ctcttttatc ttgcttggtt     360
tcgcaagcgg tgttcttggt atcactttgt gcttccatag gtgtcttact catggcggtt     420
tcaagcttcc taagttggtt gagtacttct ttgcctactg tggctctctc gctcttcagg     480
gagatcccat ggaatgggtg agcaaccata ggtaccatca ccagttcgtc gatacagaaa     540
gagatgttca tagtccaact caaggatttt ggttctgtca cattggttgg gttcttgaca     600
aagatttatt cgtcgaaaaa cgtggtggcc gaagaaacaa tgtgaatgat ttgaagaaac     660
aagccttcta cagattcctc cagaaaactt atatgtacca tcaattggct ctaatagctc     720
tactttacta cgtcggaggg tttccataca ttgtctgggg aatgggtttt agattggtgt     780
ttatgttcca ttccactttc gctatcaact cagtttgtca taaatggggc ggaaggccat     840
ggaatactgg agatttatcg accaacaata tgtttgttgc attgtgtgcg tttggagagg     900
gctggcataa caaccaccac gcattcgaac aatcagctcg acacgggcta gaatggtggc     960
agatcgatgt tacttggtac gttatcagga ctctacaagc tattggattg ctaccaatg    1020
tgaagctacc aactgaagct cagaagcaaa agctcaaagc aaagagtgcc taaggagttt    1080
gaagcatgta ataagtgttt gtattcgata cctacttata tatgtttcta gagtcgtacg    1140
tgtaatgaat aaagttcgag gcagctatat agactgtgtt cggatatgaa atcgttgta     1200
ttcttgtatc tgatcgaaaa tagctgcctt gataggtgtt cgataaaaca ttgttatgtt    1260
gcttggtgta gttgtgtggg tcttgctttg tactgtattg tgttgtgtca cgttttgaga    1320
ttatatatag ttttcttgtg ttcaaaaaaa aaaaa                               1355
```

<210> SEQ ID NO 2
<211> LENGTH: 356
<212> TYPE: PRT
<213> ORGANISM: Limnanthes douglasii

<400> SEQUENCE: 2

```
Leu Arg Leu Ser Leu Tyr Phe Pro Ile Ser Ile Ser Leu Ser Leu Ser
1               5                   10                  15

Leu Glu Ala Met Ala Ser Phe Ile Ala Thr Thr Thr Pro Ala Met Pro
                20                  25                  30

Ala Phe Ala Ser Val Leu Asp Pro Lys Ile Pro Thr Lys Pro Glu Pro
            35                  40                  45

Lys Thr Glu Thr Pro Lys Pro Lys Asp Asp Leu Glu Arg Phe Arg Thr
        50                  55                  60

Ser Glu Val Val Leu Glu Arg Lys Ser Lys Gly Phe Trp Arg Arg Lys
65                  70                  75                  80

Trp Asn Pro Arg Asp Ile Gln Asn Ala Val Thr Leu Val Leu His
                85                  90                  95

Ala Leu Ala Ala Met Ala Pro Phe Tyr Phe Ser Trp Asp Ala Phe Trp
            100                 105                 110

Ile Ser Phe Ile Leu Leu Gly Phe Ala Ser Gly Val Leu Gly Ile Thr
        115                 120                 125
```

-continued

```
Leu Cys Phe His Arg Cys Leu Thr His Gly Gly Phe Lys Leu Pro Lys
    130                 135                 140

Leu Val Glu Tyr Phe Phe Ala Tyr Cys Gly Ser Leu Ala Leu Gln Gly
145                 150                 155                 160

Asp Pro Met Glu Trp Val Ser Asn His Arg Tyr His His Gln Phe Val
                165                 170                 175

Asp Thr Glu Arg Asp Val His Ser Pro Thr Gln Gly Phe Trp Phe Cys
            180                 185                 190

His Ile Gly Trp Val Leu Asp Lys Asp Leu Phe Val Glu Lys Arg Gly
        195                 200                 205

Gly Arg Arg Asn Asn Val Asn Asp Leu Lys Lys Gln Ala Phe Tyr Arg
    210                 215                 220

Phe Leu Gln Lys Thr Tyr Met Tyr His Gln Leu Ala Leu Ile Ala Leu
225                 230                 235                 240

Leu Tyr Tyr Val Gly Gly Phe Pro Tyr Ile Val Trp Gly Met Gly Phe
                245                 250                 255

Arg Leu Val Phe Met Phe His Ser Thr Phe Ala Ile Asn Ser Val Cys
            260                 265                 270

His Lys Trp Gly Gly Arg Pro Trp Asn Thr Gly Asp Leu Ser Thr Asn
        275                 280                 285

Asn Met Phe Val Ala Leu Cys Ala Phe Gly Glu Gly Trp His Asn Asn
    290                 295                 300

His His Ala Phe Glu Gln Ser Ala Arg His Gly Leu Glu Trp Trp Gln
305                 310                 315                 320

Ile Asp Val Thr Trp Tyr Val Ile Arg Thr Leu Gln Ala Ile Gly Leu
                325                 330                 335

Ala Thr Asn Val Lys Leu Pro Thr Glu Ala Gln Lys Gln Lys Leu Lys
            340                 345                 350

Ala Lys Ser Ala
        355

<210> SEQ ID NO 3
<211> LENGTH: 305
<212> TYPE: PRT
<213> ORGANISM: Arabidopsis thaliana

<400> SEQUENCE: 3

Met Ser Leu Ser Ala Ser Glu Lys Glu Asn Asn Lys Lys Met Ala
  1               5                  10                  15

Ala Asp Lys Ala Glu Met Gly Arg Lys Lys Arg Ala Met Trp Glu Arg
            20                  25                  30

Lys Trp Lys Arg Leu Asp Ile Val Lys Ala Phe Ala Ser Leu Phe Val
        35                  40                  45

His Phe Leu Cys Leu Leu Ala Pro Phe Asn Phe Thr Trp Pro Ala Leu
    50                  55                  60

Arg Val Ala Leu Ile Val Tyr Thr Val Gly Leu Gly Ile Thr Val
 65                  70                  75                  80

Ser Tyr His Arg Asn Leu Ala His Arg Ser Phe Lys Val Pro Lys Trp
                85                  90                  95

Leu Glu Tyr Phe Phe Ala Tyr Cys Gly Leu Leu Ala Ile Gln Gly Asp
            100                 105                 110

Pro Ile Asp Trp Val Ser Thr His Arg Tyr His His Gln Phe Thr Asp
        115                 120                 125

Ser Asp Arg Asp Pro His Ser Pro Asn Glu Gly Phe Trp Phe Ser His
    130                 135                 140
```

```
Leu Leu Trp Leu Phe Asp Thr Gly Tyr Leu Val Glu Lys Cys Gly Arg
145                 150                 155                 160

Arg Thr Asn Val Glu Asp Leu Lys Arg Gln Trp Tyr Tyr Lys Phe Leu
                165                 170                 175

Gln Arg Thr Val Leu Tyr His Ile Leu Thr Phe Gly Phe Leu Leu Tyr
            180                 185                 190

Tyr Phe Gly Gly Leu Ser Phe Leu Thr Trp Gly Met Gly Ile Gly Val
        195                 200                 205

Ala Met Glu His His Val Thr Cys Leu Ile Asn Ser Leu Cys His Val
    210                 215                 220

Trp Gly Ser Arg Thr Trp Lys Thr Asn Asp Thr Ser Arg Asn Val Trp
225                 230                 235                 240

Trp Leu Ser Val Phe Ser Phe Gly Glu Ser Trp His Asn Asn His His
                245                 250                 255

Ala Phe Glu Ser Ser Ala Arg Gln Gly Leu Glu Trp Trp Gln Ile Asp
            260                 265                 270

Ile Ser Trp Tyr Ile Val Arg Phe Leu Glu Ile Ile Gly Leu Ala Thr
        275                 280                 285

Asp Val Lys Leu Pro Ser Glu Ser Gln Arg Arg Arg Met Ala Met Val
    290                 295                 300

Arg
305

<210> SEQ ID NO 4
<211> LENGTH: 1807
<212> TYPE: DNA
<213> ORGANISM: Limnanthes douglasii
<220> FEATURE:
<221> NAME/KEY: unsure
<222> LOCATION: (302)..(303)
<221> NAME/KEY: unsure
<222> LOCATION: (312)
<221> NAME/KEY: unsure
<222> LOCATION: (315)
<221> NAME/KEY: unsure
<222> LOCATION: (421)
<221> NAME/KEY: unsure
<222> LOCATION: (1727)

<400> SEQUENCE: 4
ctcactctca cacctccttc tctctctttg tcggcttctc cggcgagata ctcaacggat    60
tcaatcgaag ggtagtacaa tatgtcggag acaaaacctg agaaaccttt gatcgcaacc   120
gtgaaaaaca cactacctga tttaaaacta tcaataaact taaaacacgt gaaactcggt   180
taccattacc tgatcaccca tggaatgtac ctgtgtctcc ctcctctcgc actagtcctc   240
ttcgctcaaa tctcaacttt gtccctcaaa gatttcaacg acatctggga acagcttcag   300
tnnaatctca tntcngtcgt tgtttcatca acacttcttg tctccttact tatccttttac  360 ttcatgactc gtccgaggcc ggtttatttg atggatttcg cgtgctataa acccgacgaa   420
nctcgaaaat ctactagaga acattttatg aagtgtggtg agagtttggg ctcttttacg   480
gaggataata tcgattttca gaggaaatta gtcgcacgat ctggacttgg tgatgctacg   540
tatttacctg aagctatcgg tactatcccg gctcatccgt cgatgaaagc tgcgagaaga   600
gaagctgagt tggtgatgtt tggtgcgatt gatcaacttt ggagaagac aaaggtgaat    660 ccgaaggata tagggatctt ggttgttaat tgcagcctgt ttagtccgac tccgtccctc   720
tcgtcgatga ttgttaacca ctataaactc cgtgggaaca ttataagcta caatctaggc   780
```

-continued

```
ggaatgggtt gcagtgctgg tttaatttcg gtcgacttag ctaaaagact tctcgagaca      840
aatccaaaca cttacgcttt agttatgagc actgaaaata tcacactaaa ctggtacatg      900
ggcaatgacc ggtccaaact cgtgtccaat tgtcttttcc ggatgggagg agctgcggtc      960
ttgttatcaa acaaaacctc tgataagaaa agatcgaagt atcagttggt tactaccgtc     1020
cgaagccaca aggtgctgac gataattgc tacggttgca tattccaaga agaagactcc      1080
aacggcaaaa tcggtgtaag cctctccaaa aatctaatgg cggtcgcagg ggacgcgctt     1140
aagactaaca tcacgacgct tggtccgttg gttttaccaa tgtcggaaca acttttgttt     1200
ttcgccacgc tggttgctcg aaaagttttc aagaagaaaa ttaagcccta cattccggac     1260
tttaaactag cttttgatca tttctgtatt catgcgggtg gtcgagctgt tttggacgag     1320
cttgagaaga atttgcagtt gtcaagctgg catctagagc cgtcgagaat gacgtttatc     1380
cggtttggta atacgtcgag tagtactttg tggtacgagc tggcgtattc ggaagccaaa     1440
gggaggatta gaaaggaga aagagtttgg cagatagggt ttggttctgg gtttaaatgt     1500
aatagtgctg tctggaaagc cttaaagagc gttgatccaa agaaagagaa caatccatgg     1560
atggatgaga tccaccagtt tccggttgct gttgtctaag gttgtgtttt gatgtttaat     1620
gtttggtgtg ttgatgcttg ctaattggtt agtgtaagaa gtacttggtt gctgctgttt     1680
caattactaa ctaaagagag tgttgaataa gcatagaaca aagtaantaa ctggaaagtg     1740
ctttgttgtt tgttcagtaa ctctattact gctgaatttc tctcaagaga agaattatgt     1800
ttaaaaa                                                               1807
```

<210> SEQ ID NO 5
<211> LENGTH: 505
<212> TYPE: PRT
<213> ORGANISM: Limnanthes douglasii
<220> FEATURE:
<221> NAME/KEY: UNSURE
<222> LOCATION: (74)
<221> NAME/KEY: UNSURE
<222> LOCATION: (77)
<221> NAME/KEY: UNSURE
<222> LOCATION: (114)

<400> SEQUENCE: 5

```
Met Ser Glu Thr Lys Pro Glu Lys Pro Leu Ile Ala Thr Val Lys Asn
1               5                   10                  15

Thr Leu Pro Asp Leu Lys Leu Ser Ile Asn Leu Lys His Val Lys Leu
                20                  25                  30

Gly Tyr His Tyr Leu Ile Thr His Gly Met Tyr Leu Cys Leu Pro Pro
            35                  40                  45

Leu Ala Leu Val Leu Phe Ala Gln Ile Ser Thr Leu Ser Leu Lys Asp
        50                  55                  60

Phe Asn Asp Ile Trp Glu Gln Leu Gln Xaa Asn Leu Xaa Ser Val Val
65                  70                  75                  80

Val Ser Ser Thr Leu Leu Val Ser Leu Leu Ile Leu Tyr Phe Met Thr
                85                  90                  95

Arg Pro Arg Pro Val Tyr Leu Met Asp Phe Ala Cys Tyr Lys Pro Asp
                100                 105                 110

Glu Xaa Arg Lys Ser Thr Arg Glu His Phe Met Lys Cys Gly Glu Ser
            115                 120                 125

Leu Gly Ser Phe Thr Glu Asp Asn Ile Asp Phe Gln Arg Lys Leu Val
        130                 135                 140

Ala Arg Ser Gly Leu Gly Asp Ala Thr Tyr Leu Pro Glu Ala Ile Gly
```

```
                145                 150                 155                 160
Thr Ile Pro Ala His Pro Ser Met Lys Ala Arg Arg Glu Ala Glu
                    165                 170                 175
Leu Val Met Phe Gly Ala Ile Asp Gln Leu Leu Glu Lys Thr Lys Val
                180                 185                 190
Asn Pro Lys Asp Ile Gly Ile Leu Val Val Asn Cys Ser Leu Phe Ser
                195                 200                 205
Pro Thr Pro Ser Leu Ser Ser Met Ile Val Asn His Tyr Lys Leu Arg
            210                 215                 220
Gly Asn Ile Ile Ser Tyr Asn Leu Gly Gly Met Gly Cys Ser Ala Gly
225                 230                 235                 240
Leu Ile Ser Val Asp Leu Ala Lys Arg Leu Leu Glu Thr Asn Pro Asn
                245                 250                 255
Thr Tyr Ala Leu Val Met Ser Thr Glu Asn Ile Thr Leu Asn Trp Tyr
                260                 265                 270
Met Gly Asn Asp Arg Ser Lys Leu Val Ser Asn Cys Leu Phe Arg Met
                275                 280                 285
Gly Gly Ala Ala Val Leu Leu Ser Asn Lys Thr Ser Asp Lys Lys Arg
            290                 295                 300
Ser Lys Tyr Gln Leu Val Thr Thr Val Arg Ser His Lys Gly Ala Asp
305                 310                 315                 320
Asp Asn Cys Tyr Gly Cys Ile Phe Gln Glu Glu Asp Ser Asn Gly Lys
                325                 330                 335
Ile Gly Val Ser Leu Ser Lys Asn Leu Met Ala Val Ala Gly Asp Ala
            340                 345                 350
Leu Lys Thr Asn Ile Thr Thr Leu Gly Pro Leu Val Leu Pro Met Ser
            355                 360                 365
Glu Gln Leu Leu Phe Phe Ala Thr Leu Val Ala Arg Lys Val Phe Lys
        370                 375                 380
Lys Lys Ile Lys Pro Tyr Ile Pro Asp Phe Lys Leu Ala Phe Asp His
385                 390                 395                 400
Phe Cys Ile His Ala Gly Gly Arg Ala Val Leu Asp Glu Leu Glu Lys
                405                 410                 415
Asn Leu Gln Leu Ser Ser Trp His Leu Glu Pro Ser Arg Met Thr Phe
            420                 425                 430
Ile Arg Phe Gly Asn Thr Ser Ser Ser Thr Leu Trp Tyr Glu Leu Ala
        435                 440                 445
Tyr Ser Glu Ala Lys Gly Arg Ile Arg Lys Gly Glu Arg Val Trp Gln
    450                 455                 460
Ile Gly Phe Gly Ser Gly Phe Lys Cys Asn Ser Ala Val Trp Lys Ala
465                 470                 475                 480
Leu Lys Ser Val Asp Pro Lys Lys Glu Asn Asn Pro Trp Met Asp Glu
                485                 490                 495
Ile His Gln Phe Pro Val Ala Val Val
            500                 505

<210> SEQ ID NO 6
<211> LENGTH: 844
<212> TYPE: DNA
<213> ORGANISM: Limnanthes douglasii

<400> SEQUENCE: 6
acacgggcaa tgaccgatcg aaactcgtgt ctaattgtct tttccgtatg ggaggagctg      60 cggtttttatt atcaaacaaa cattcggaca aaaaacgatc gaaataccag ttggttacta     120
```

-continued

```
ccgtccgaag ccacaaaggt gctgacgata aattgctatgg ctgcatcttt caagaagagg    180
actcgactgg aataagtggt gtaagtctct cgaaaaatct aatggcagtc gcaggcgatg    240
cactcaagac aaacatcacg acgatcggtc cgttagtttt accaatgact gaacaacttt    300
tgtattttgc ctccttggtc ggccgaaata ttttcaaaat gaaataaaa acctacgttc     360 ccgattttaa actcgccttc gagcatttct gtattcacgc aggtggtcga ggagtgttgg    420
acgcgctgga agaaatttg cagttgtcgg agtggcatct tgagccatcg aggatgacgt     480
tgtaccgatt tggtaatacg tcgagtagta gtttatggta tgagctggcg tattcggaag    540
ccaaagggag aattaagaag ggagagaggg tttggcagat agggtttggt tcagggttta    600
agtgtaatag tgtggtttgg aaagcgctac ggacagtaga tccgaaggaa gagaataatc    660
cttggacgga tgagatccac cagtttccag ttgctgttgt ctgagtttat gttggatgtt    720
tgaagtaaac ttaatgtttt ggtctggtgt ccatgctgag attagtgcag caactctttt    780
gcgaaataat aaatgcttag aaactgtttt gttgtttaaa aaaaaaaaa aaaaaaaaa      840 aaaa                                                                  844
```

<210> SEQ ID NO 7
<211> LENGTH: 233
<212> TYPE: PRT
<213> ORGANISM: Limnanthes douglasii

<400> SEQUENCE: 7

```
Thr Gly Asn Asp Arg Ser Lys Leu Val Ser Asn Cys Leu Phe Arg Met
1               5                  10                  15

Gly Gly Ala Ala Val Leu Leu Ser Asn Lys His Ser Asp Lys Lys Arg
            20                  25                  30

Ser Lys Tyr Gln Leu Val Thr Thr Val Arg Ser His Lys Gly Ala Asp
        35                  40                  45

Asp Asn Cys Tyr Gly Cys Ile Phe Gln Glu Asp Ser Thr Gly Ile
    50                  55                  60

Ser Gly Val Ser Leu Ser Lys Asn Leu Met Ala Val Ala Gly Asp Ala
65                  70                  75                  80

Leu Lys Thr Asn Ile Thr Thr Ile Gly Pro Leu Val Leu Pro Met Thr
                85                  90                  95

Glu Gln Leu Leu Tyr Phe Ala Ser Leu Val Gly Arg Asn Ile Phe Lys
            100                 105                 110

Met Lys Ile Lys Thr Tyr Val Pro Asp Phe Lys Leu Ala Phe Glu His
        115                 120                 125

Phe Cys Ile His Ala Gly Gly Arg Gly Val Leu Asp Ala Leu Glu Lys
    130                 135                 140

Asn Leu Gln Leu Ser Glu Trp His Leu Glu Pro Ser Arg Met Thr Leu
145                 150                 155                 160

Tyr Arg Phe Gly Asn Thr Ser Ser Ser Leu Trp Tyr Glu Leu Ala
                165                 170                 175

Tyr Ser Glu Ala Lys Gly Arg Ile Lys Lys Gly Glu Arg Val Trp Gln
            180                 185                 190

Ile Gly Phe Gly Ser Gly Phe Lys Cys Asn Ser Val Val Trp Lys Ala
        195                 200                 205
```

```
-continued

Leu Arg Thr Val Asp Pro Lys Glu Glu Asn Asn Pro Trp Thr Asp Glu
    210                 215                 220

Ile His Gln Phe Pro Val Ala Val Val
225                 230
```